(12) United States Patent
Stott et al.

(10) Patent No.: US 7,288,072 B2
(45) Date of Patent: Oct. 30, 2007

(54) USER INTERFACE FOR AUTOMATED DIAGNOSTIC HEARING TEST

(75) Inventors: Kenneth R. Stott, Sugar Land, TX (US); Robert L. Stott, Sugar Land, TX (US)

(73) Assignee: Tympany, Inc., Salt Lake City, UT (US)

( * ) Notice: Subject to any disclaimer, the term of this patent is extended or adjusted under 35 U.S.C. 154(b) by 78 days.

(21) Appl. No.: 10/663,225

(22) Filed: Sep. 16, 2003

(65) Prior Publication Data

US 2004/0152998 A1 Aug. 5, 2004

Related U.S. Application Data

(63) Continuation-in-part of application No. 10/439,958, filed on May 15, 2003.

(60) Provisional application No. 60/466,313, filed on Apr. 29, 2003, provisional application No. 60/383,303, filed on May 23, 2002.

(51) Int. Cl.
*A61B 5/00* (2006.01)
(52) U.S. Cl. .................................... 600/559
(58) Field of Classification Search ............... 600/300, 600/301, 559; 73/585; 128/920; 702/182–189; 351/223; 704/224; 434/169, 308; 446/397
See application file for complete search history.

(56) References Cited

U.S. PATENT DOCUMENTS

| | | | |
|---|---|---|---|
| 3,134,861 A | 5/1964 | Dempsey | |
| 5,197,332 A | 3/1993 | Shennib | |
| 5,323,468 A | 6/1994 | Bottesch | |
| 5,433,610 A * | 7/1995 | Godfrey et al. | ............. 434/169 |
| 5,645,074 A | 7/1997 | Shennib et al. | |
| 5,811,681 A | 9/1998 | Braun et al. | |
| 6,160,893 A | 12/2000 | Saunders et al. | |
| 6,168,563 B1 * | 1/2001 | Brown | ............. 600/301 |
| 6,201,875 B1 * | 3/2001 | Davis et al. | ............. 381/314 |
| 6,331,164 B1 | 12/2001 | Shaw et al. | |
| 6,366,863 B1 | 4/2002 | Bye et al. | |
| 6,377,925 B1 | 4/2002 | Greene et al. | |

(Continued)

FOREIGN PATENT DOCUMENTS

JP 05030599 A 2/1993

(Continued)

OTHER PUBLICATIONS

International Search Report, Oct. 6, 2003.

(Continued)

*Primary Examiner*—Max F. Hindenburg
*Assistant Examiner*—Brian Szmal
(74) *Attorney, Agent, or Firm*—Locke Liddell & Sapp PLLC

(57) ABSTRACT

Method and system are disclosed for a multimedia user interface for an automated diagnostic hearing test. The user interface provides a means for a patient to interact with the automated hearing test to complete each test. The patient is given instructions and guidance for every test, and can call the operator at any point for help. Warning messages and progress indicators are provided to help the patient gauge his progress. Such an arrangement allows the patient to test his own hearing with minimal or no assistance from an audiologist or other hearing health professional. The user interface also allows the operator to configure the automated hearing test as needed.

49 Claims, 19 Drawing Sheets

U.S. PATENT DOCUMENTS

| | | | |
|---|---|---|---|
| 6,379,314 B1 | 4/2002 | Horn | |
| 6,396,930 B1 | 5/2002 | Vaudrey et al. | |
| 6,416,482 B1 | 7/2002 | Braun et al. | |
| 6,428,485 B1* | 8/2002 | Rho | 600/559 |
| 6,447,461 B1 | 9/2002 | Eldon | |
| 6,496,585 B1 | 12/2002 | Margolis | |
| 6,644,120 B1 | 11/2003 | Braun et al. | |
| 6,647,345 B2 | 11/2003 | Bye et al. | |
| 6,674,862 B1 | 1/2004 | Magilen | |
| 6,730,041 B2* | 5/2004 | Dietrich | 600/558 |
| 7,149,684 B1* | 12/2006 | Ahroon | 704/224 |
| 2002/0016554 A1 | 2/2002 | Iseberg | |
| 2002/0026125 A1 | 2/2002 | Leysieffer | |
| 2002/0068986 A1 | 6/2002 | Mouline | |
| 2002/0076056 A1 | 6/2002 | Pavlakos | |
| 2002/0107692 A1 | 8/2002 | Litovsky | |
| 2002/0136365 A1 | 9/2002 | D'Agri | |
| 2002/0165466 A1 | 11/2002 | Givens et al. | |
| 2003/0083591 A1 | 5/2003 | Edwards et al. | |
| 2004/0006283 A1 | 1/2004 | Harrison et al. | |
| 2004/0039299 A1 | 2/2004 | Harrison et al. | |
| 2004/0049125 A1 | 3/2004 | Nakamura | |
| 2004/0064066 A1 | 4/2004 | John et al. | |
| 2004/0068200 A1 | 4/2004 | Harrison et al. | |
| 2004/0071295 A1 | 4/2004 | Wasden et al. | |
| 2004/0071296 A1 | 4/2004 | Wasden et al. | |
| 2004/0073134 A1 | 4/2004 | Wasden et al. | |
| 2004/0073135 A1* | 4/2004 | Wasden et al. | 600/559 |
| 2004/0073136 A1 | 4/2004 | Thorton et al. | |
| 2004/0097826 A1 | 5/2004 | Harrison et al. | |
| 2004/0152998 A1 | 8/2004 | Stott et al. | |
| 2005/0033193 A1 | 2/2005 | Wasden et al. | |

FOREIGN PATENT DOCUMENTS

| | | |
|---|---|---|
| NL | 8400196 | 8/1984 |
| WO | WO9841973 | 9/1998 |
| WO | WO0106916 | 2/2001 |
| WO | WO02062221 | 8/2002 |

OTHER PUBLICATIONS

Gerald A. Studebaker, et al., *Frequency-Importance and Transfer Functions for Recorded CID W-22 Word Lists*, Journal of Speech and Hearing Research: Apr. 1991, pp. 427-438; vol. 34.

Aaron R. Thornton, et al., *Speech-Discrimination Scores Modeled as a Binomial Variable*, Journal of Speech and Hearing Research, Sep. 1978, pp. 507-518; vol. 21, No. 3.

Chris Haplin, Ph.D., et al., *The articulation index in clinical diagnosis and hearing aid fitting*, Current Opinion in Otolaryngology & Head and Neck Surgery, 1996, pp. 325-334; Rapid Science Publishers.

*The Audiology Primer for Students and Health Care Professionals*; Summer, 1997, pp. i-69; Department of Veterans Affairs.

International Search Report for PCT/US03/16200 dated Jul. 28, 2004.

International Search Report for PCT/US04/15329 dated Nov. 16, 2004.

International Search Report for PCT/US04/15328 dated Nov. 19, 2004.

Gelfand, S.A., *Essentials of Audiology*, 2d ed., Thieme Medical Publishers, Inc., 2001.

McCullough et al., *A multimedia approach for estimating speech recognition of multilingual clients*, AJA, Mar. 1994, pp. 19-22.

Matsuhira, Toshimasa, *Improved method of masking in pure tone audiometry—use of minimum level masking*, Practica Oto-Rhino-Laryngologica, 82:11; 1541-1540, 1989.

Smith, Brenda L. and Markides, Andreas, *Interaural attenuation for pure tones and speech*, British Journal of Audiology, 15:40 9-54, 1981.

Thornton, Aaron, *Computer-Assisted Audiometry and Technicians in a High-Volume Practice*, Nov. 1993 AJA, pp. 11-13.

Barry, S. Joseph, *Can Bone Conduction Thresholds Really Be Poorer Than Air?*, Nov. 1994 AJA, pp. 21-22.

M.S. Dean and F.N. Martin, *Insert Earphone Depth and the Occlusion Effect*, AJA, vol. 9, 159-0889, Sep. 5, 2000.

J.A. McCullough, R.H. Wilson, J.D. Birck and L.G. Anderson, *A Multimedia Approach for Estimating Speech Recognition of Multilingual Clients*, Mar. 1994 AJA, pp. 19-22.

R.H. Wilson and J.K. Antablin, *A Picture Identification Task as an Estimate of the Word-Recognition Performance of Nonverbal Adults*, Journal of Speech and Hearing Disorders, May 1980, vol. 45, No. 2.

* cited by examiner

520

```
Otogram Configuration
| Input Screen | Paging Encoder Interface | Paging Options | Machine Options | Reporting Options | Network Options | Test Options |
```

522
☑ [Paging Encoder is Attached]

524 {
- Communications Port: [1]
- Encoder ID: [WaveWare Paging Encoder]
- Encoder Timeout: [500]

- Pager CapCode: [0000100]
- Pager Data Rate: [5]
}

[Save] [Exit]

```
Otogram Configuration
| Input Screen | Paging Encoder Interface | Paging Options | Machine Options | Reporting Options | Network Options | Test Options |
```

Page Format [%N-Patent Name, %T-Test Name.]

532 — ☑ Page Administrator at end of testing session — [%N's Otogram is completed.]
534 — ☐ Page Administrator at end of each test — [%N has completed the %T test.]
536 — ☑ Page Administrator after inactivity threshold — [%N is not progressing through the %T test.]
  Inactivity Threshold (in seconds) [120]          } 539
538 — ☑ Page Administrator after inability to reach pure tone threshold — [%N is not progressing through the %T test.]
  Inability Threshold (in seconds) [360]

540
Paging Device: [Radio ▼]

Network Paging Drop: [           ]

[Save and Exit] [Exit]

USER INTERFACE FOR AUTOMATED DIAGNOSTIC HEARING TEST

CROSS-REFERENCE TO RELATED APPLICATION

This application for patent claims the benefit of priority from, and hereby incorporates by reference, U.S. Provisional Patent Application Ser. No. 60/466,313, entitled "System and Method for Conducting Multiple Diagnostic Hearing Tests," filed on Apr. 29, 2003, and is a continuation-in-part of U.S. patent application Ser. No. 10/439,958, entitled "Automated Diagnostic Hearing Test," filed on May 15, 2003, which is also hereby incorporated by reference. U.S. patent application Ser. No. 10/439,958 claims the benefit of priority from, and incorporates by reference, U.S. Provisional Patent Application Ser. No. 60/383,303, entitled "Audiometer," and filed on May 23, 2002, and U.S. Provisional Patent Application Ser. No. 60/466,313, entitled "System and Method for Conducting Multiple Diagnostic Hearing Tests," filed on Apr. 29, 2003.

BACKGROUND OF THE INVENTION

1. Field of the Invention

This invention is directed in general to the field of audiology and in particular to a user interface for an automated method and system of assessing and analyzing hearing loss.

2. Description of the Related Art

According to recent studies, over 20 million people in the United States alone have some degree of hearing loss. The number of people worldwide who have some degree of hearing loss is estimated to be much greater. Not surprisingly, many of these people are unaware that they have suffered a decrease in hearing capacity. The decreased hearing capacity may be due to several factors, including age, health, occupation, injury, and disease. This loss of hearing can lead to significant reductions in quality of life, impaired relationships, reduced access to employment and diminished productivity. Failure to treat the hearing loss may worsen the impact. According to the Better Hearing Institute, the annual cost in the United States in terms of lost productivity, special education, and medical care because of untreated hearing loss is approximately $56 billion. Much of this staggering cost can be reduced or prevented by early detection and treatment. Unfortunately, few people obtain regular and frequent hearing tests as a part of their routine healthcare due, in part, to the lack of a simple, convenient, and relatively inexpensive hearing test.

Traditionally, a hearing test is conducted in a clinical setting by a hearing health professional, such as an audiologist, who administers the hearing test manually. The hearing health professional controls an audiometer to produce a series of tones that each have a very specific frequency and intensity. The term "intensity" as used herein refers to the amplitude of the tone and is usually stated in decibels (dB). The tones are then conducted through a transducer, such as earphones or ear inserts, to the patient in a quiet room or sound isolation booth. For each audible tone, the patient gestures or otherwise indicates that he has heard the tone. If the tone is not audible, the patient does not respond. The hearing health professional thereafter adjusts the intensity level of the tone in preset increments until it becomes audible to the patient. By repeating this process for several different tones and compiling the results, the hearing health professional is able to determine the extent of the hearing loss, if any.

An advantage of having a hearing health professional manually administer the hearing test is the hearing health professional can apply his considerable training and experience during the test. For example, by simply talking to the patient and varying the loudness of his voice, the hearing health professional can determine an initial intensity level at which to start the tones and sounds. Furthermore, the hearing health professional can adapt the pace of the test as needed to accommodate a tired or uncooperative patient. More importantly, the hearing health professional can discern between false responses or guesses and responses that are legitimate. Finally, the hearing health professional can adjust the results of the hearing test as needed to reflect extenuating circumstances or problems, such as excessive ambient noise, equipment limitations, and other similar factors.

Like most highly trained and specialized medical professionals, however, a hearing health professional's time and services are usually very expensive. Accessibility and convenience can also be issues, as there are fewer hearing health professionals relative to other types of medical professionals. And while hearing health professionals are highly trained, they are limited in their ability to make rapid and accurate calculations of the test data and have to rely on approximations and rules of thumb for guidance in many instances. In addition, few hearing health professionals in the United States can speak a foreign language. As a result, traditional hearing tests are almost always administered in English, which can present a problem for non-English speaking patients.

Other drawbacks of the traditional, manually administered hearing tests include the need for a quiet room or sound isolation booth in order to properly conduct the tests. The quiet room or sound isolation booth has to comply with ANSI (American National Standards Institute) requirements in terms of how much noise may penetrate the room or booth during a test. Typically, a specially trained technician must evaluate and certify the quiet room or sound isolation booth as meeting ANSI standards before the room or booth can be used. At present, there are relatively few technicians who are trained to perform such evaluations and certifications. All the above factors combine to increase the complexity of the traditional hearing tests and thereby discourage or at least contribute to a general lack of interest by most people in obtaining regular and frequent hearing tests.

One attempt to simplify the traditional hearing test involves the use of a computer network, such as the Internet, to administer the test. The computer network facilitates interaction between a centralized test administration site and remotely located patient sites. Such an arrangement makes it possible (or at least more convenient) for people in remote or rural areas to obtain a hearing test. And the hearing test can be performed so that it meets standardized guidelines such as ANSI requirements or certification standards. Despite the increased convenience, a hearing health professional must still manually administer the test, albeit remotely. In this regard, the test is very similar to the traditional hearing test and has many of the same shortcomings.

Accordingly, what is needed is a hearing test that overcomes the shortcomings of the traditional hearing test. Specifically, what is needed is a hearing test, and a user interface therefor, that is simpler, more convenient, less expensive, can be administered by the patient rather than by the hearing health professional, yet does not compromise the accuracy or thoroughness of the traditional, manually administered hearing test.

SUMMARY OF THE INVENTION

The present invention is directed to a multimedia user interface for an automated diagnostic hearing test. The user interface provides a means for a patient to interact with the automated hearing test to complete each test. The patient is given instructions and guidance for every test, and can call the operator at any point for help. Warning messages and progress indicators are provided to help the patient gauge his progress. Such an arrangement allows the patient to test his own hearing with minimal or no assistance from an audiologist or other hearing health professional. The user interface also allows the operator to configure the automated hearing test as needed.

BRIEF DESCRIPTION OF THE DRAWINGS

A better understanding of the invention may be had by reference to the following detailed description when taken in conjunction with the accompanying drawings, wherein:

Figures 5D, 5E:
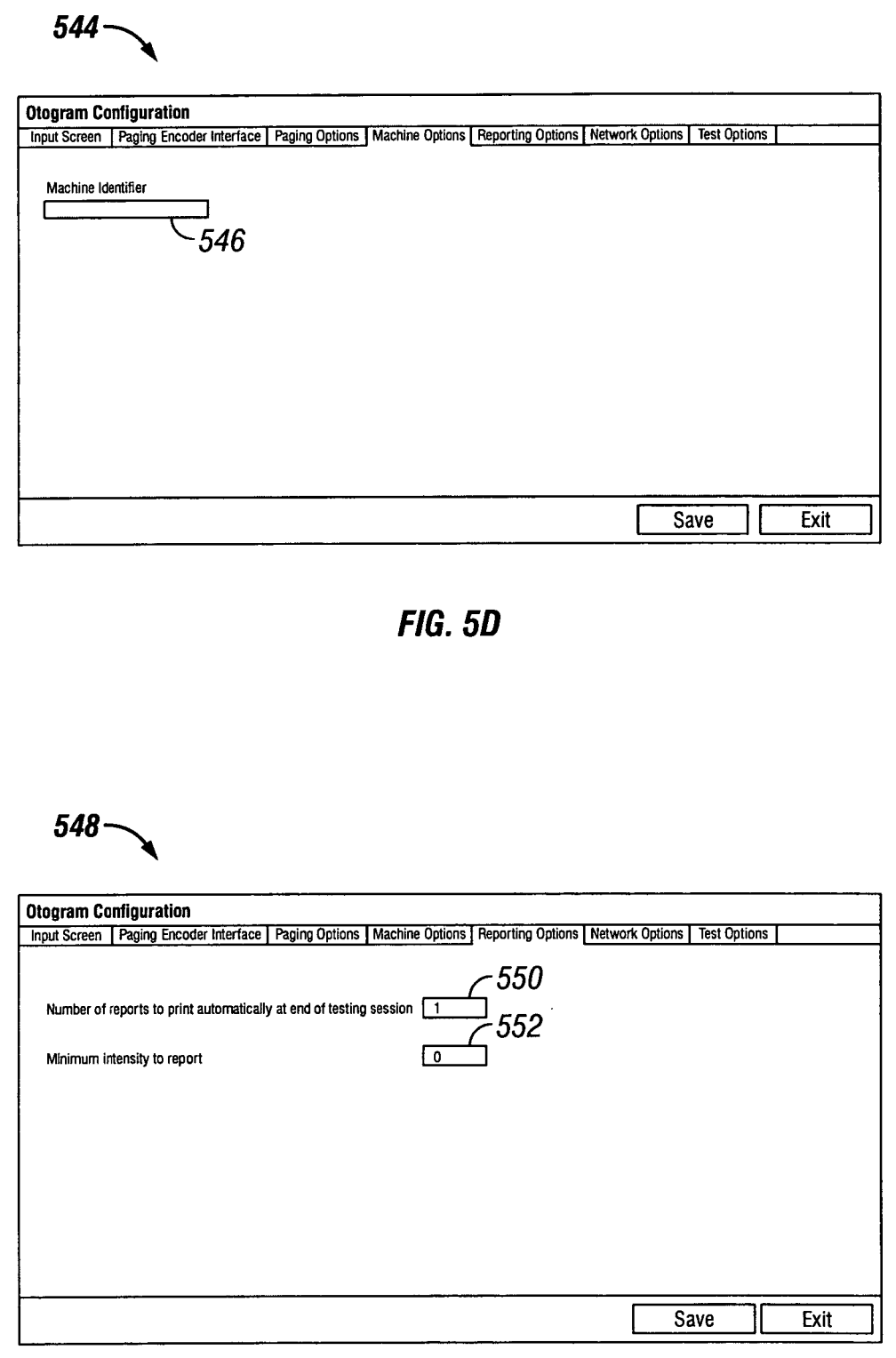
Figures 5F, 5G:
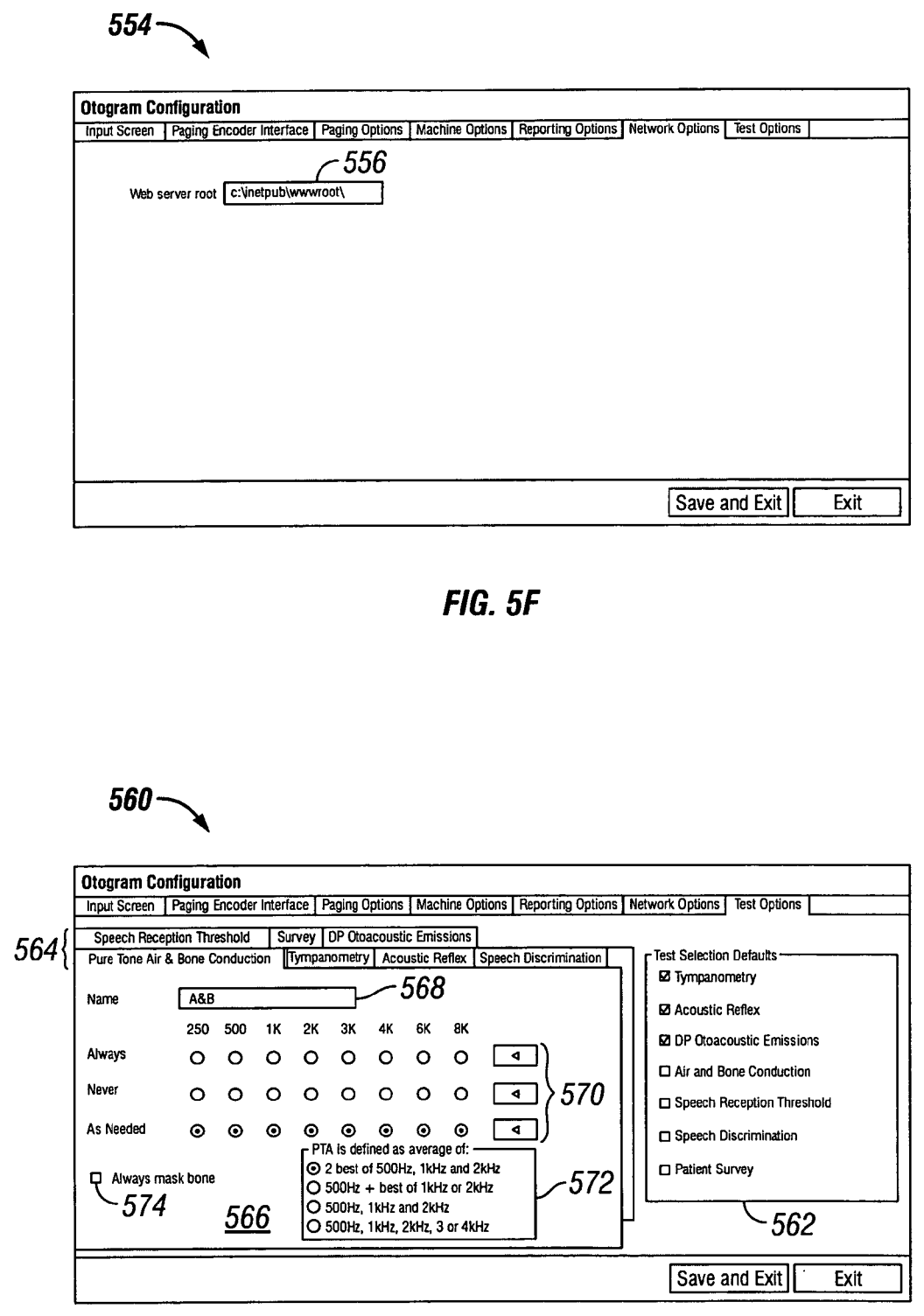
Figures 5H, 5I:
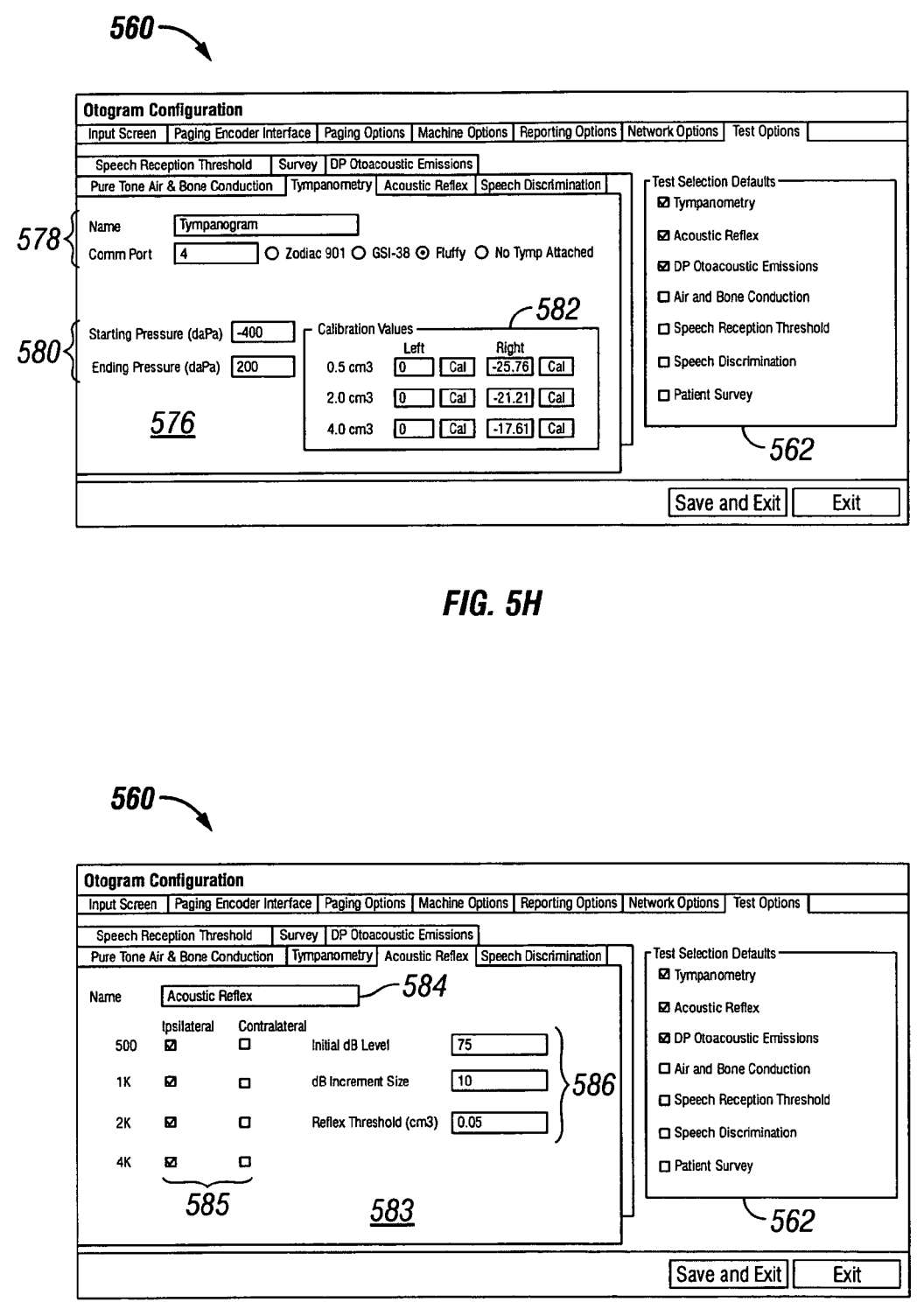
Figures 5J, 5K:
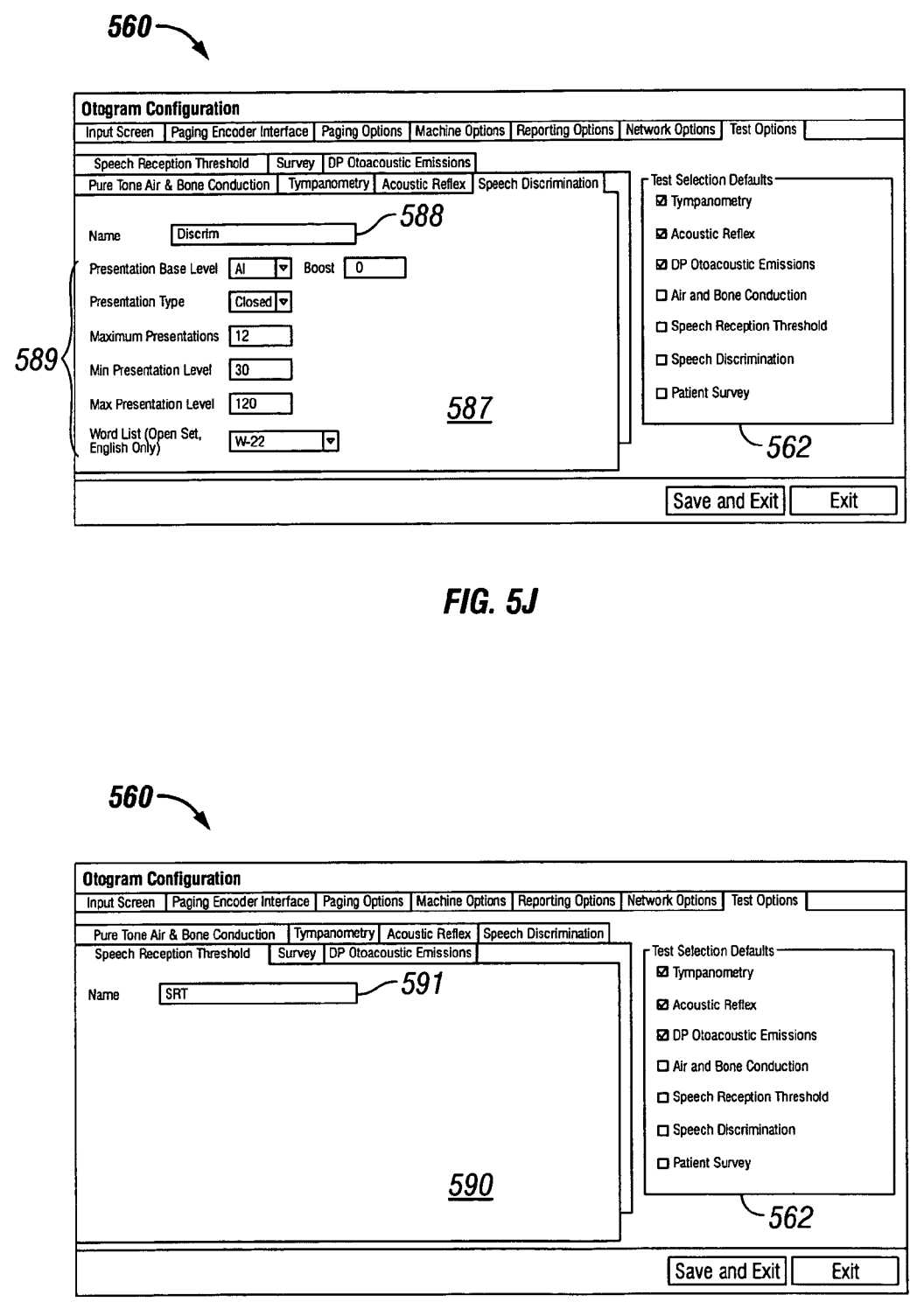
Figures 5L, 5M:
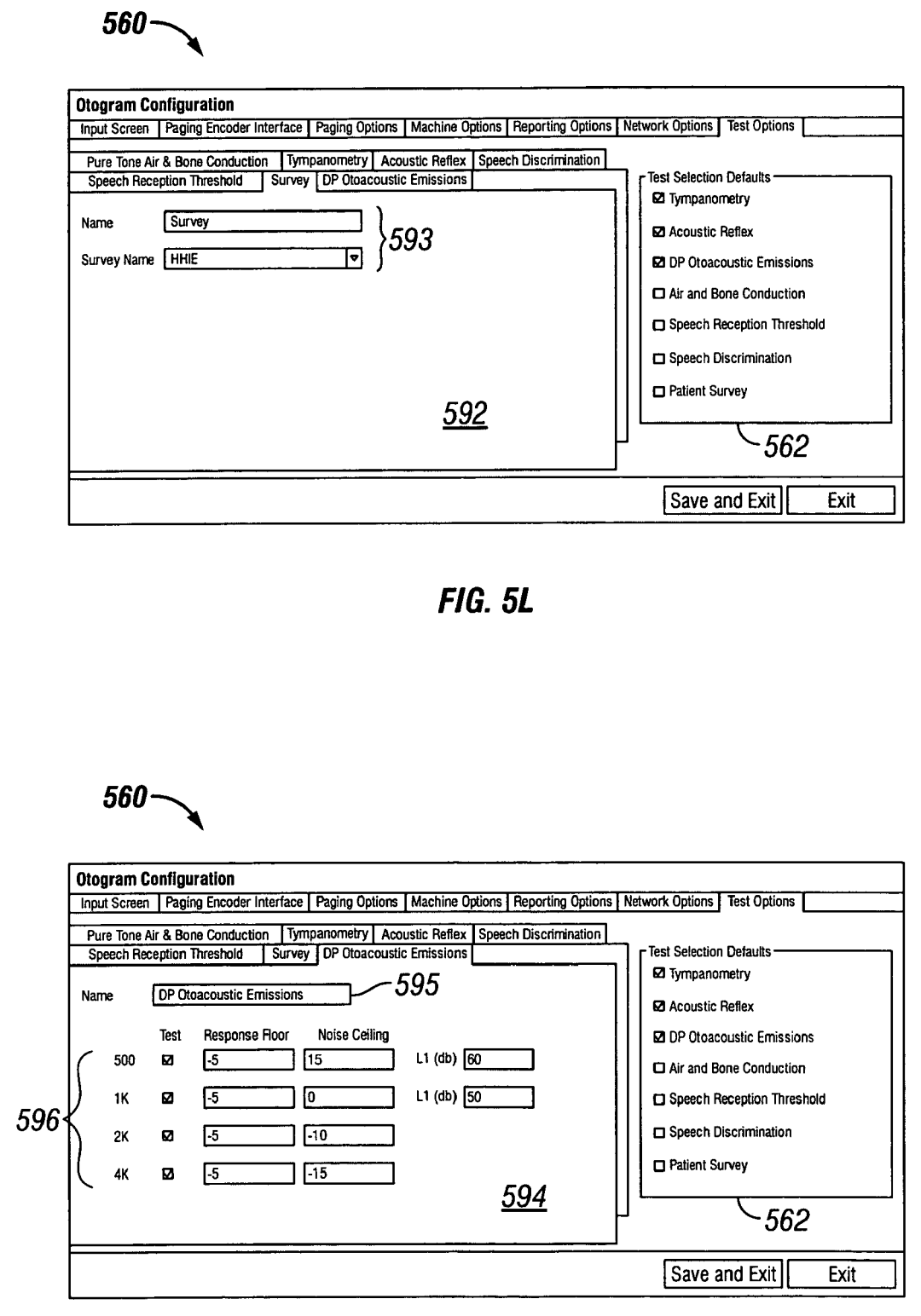

FIGS. 5A-5M illustrate an exemplary implementation of a system configuration component of the user interface according to embodiments of the invention;

DETAILED DESCRIPTION OF THE INVENTION

Figure 1:
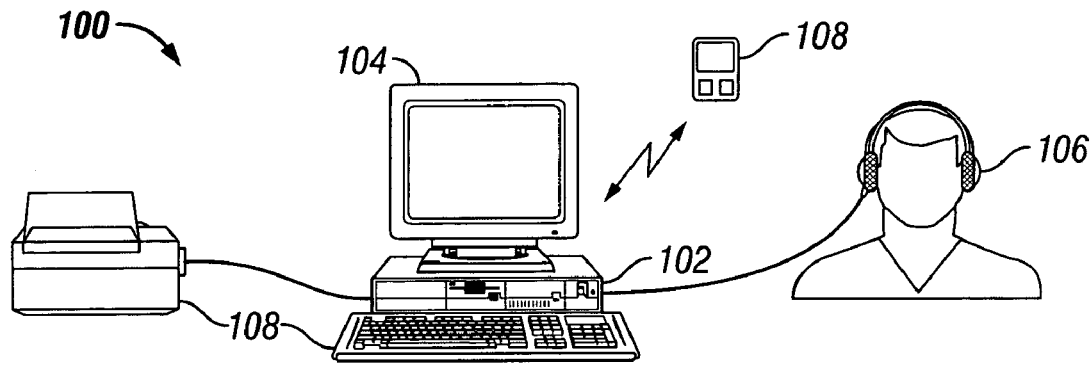
FIG. 1 illustrates an exemplary system for providing an automated hearing test according to embodiments of the invention.

Following is a detailed description of the invention with reference to the drawings wherein reference numerals for the same or similar elements are carried forward. It should be noted that unless otherwise indicated, the design and layout of the various features shown in the drawings, including the size, shape, color (or lack thereof), location, and arrangement of the various fields, checkboxes, text boxes, graphics, and other information, are provided for illustrative purposes only, and the invention is not to be limited to any particular design or layout.

As mentioned above, the present invention is directed to automated testing of a patient's hearing and, more specifically, to a user interface for such an automated hearing test. The term "automated testing" as used herein refers to testing that is performed primarily by a computer, as opposed to testing that is performed primarily by a hearing health professional. The user interface allows the patient to test his own hearing with minimal or no assistance from a hearing health professional. Typically, an operator, such as the hearing health professional or a trained administrator, helps the patient with the initial set up (e.g., seating, putting on the transducers, demonstrating button usage, etc.) and explains in general how the test works. Thereafter, the user interface instructs and prompts the patient through the remainder of the test.

Patients will realize a number of benefits from the user interface of the present invention. In general, the user interface is an intuitive, user-friendly interface that makes the automated hearing test simple to use and provides for a more pleasant and enjoyable patient experience. In addition, the user interface has a "high-tech" look and feel that inspires confidence in the patient that he is using state-of-the-art technology that will produce more accurate results. Moreover, the user interface provides a clear and consistent voice that may be easier to understand than some hearing health professionals who may speak with an accent or whose speech may otherwise be difficult to understand. Finally, the user interface allows the patient to proceed with the hearing test at his own pace, since little or no assistance is needed from the hearing health professional.

Referring now to FIG. 1, a system 100 is shown for providing automated hearing tests in which the user interface according to embodiments of the invention is used. The system 100 has three main components, namely, a computer 102, and a display screen 104, and at least one transducer 106. Other components of the system 100 that may be present include a tympanometer, keyboard, mouse, printer, paging system, and the like (indicated generally at 108). The paging system may be any suitable paging technology that uses one or more pagers 108 for alerting the operator. The one or more pagers 108 preferably can display text messages for informing the operator of the nature of the alert. Other types of paging system may also be used without departing from the scope of the invention (e.g., Internet based paging systems).

The computer 102 may be any suitable computer, from a desktop PC to a high-end workstation, as the particular type/model/brand of computer is not overly important to the practice of the invention. The display screen 104 may likewise be any suitable display screen, from a CRT to an LCD, as the particular type/model/brand of display screen is not overly significant for purposes of the present invention. In some embodiments, however, a touchscreen monitor may be easier to use than conventional CRT or LCD display screens in terms of the physical interaction between the patient and the automated hearing test.

As for the transducer 106, this component may be an ear insert, earphones, and the like for air conduction. For bone conduction, the transducer 106 may be a vibrator or other similar devices. In some cases, the transducer 106 may be mounted on a headset worn by the patient. Usually, a separate transducer is used for air conduction versus bone conduction and the transducers are swapped as need during the hearing test. Preferably, the bone conduction transducer is arranged in such a way as to allow testing of either ear without moving the transducer and without interfering with the air conduction transducer. In some embodiments, both the air conduction transducer and the bone conduction transducer are combined in a single unit. An example of such a combined unit is described in U.S. patent application Ser. No. 10/438,751, entitled "Apparatus for Bone Conduction Threshold Hearing Test," which is hereby incorporated by reference.

Figure 2:
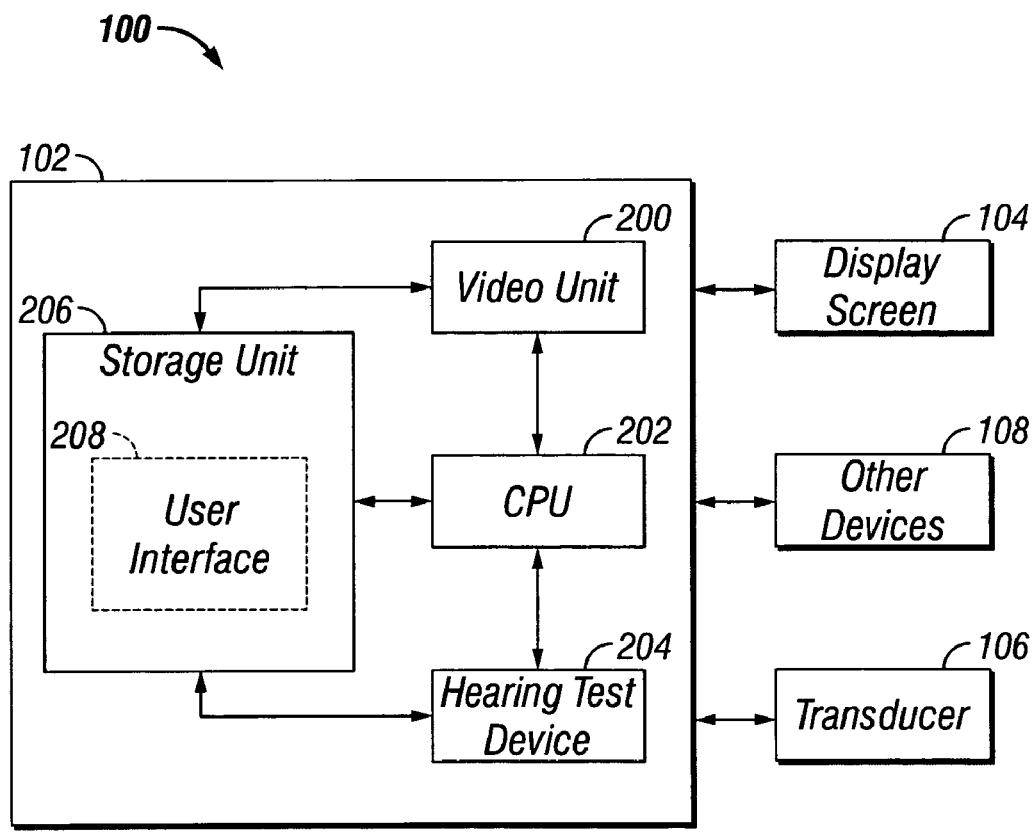
FIG. 2 illustrates a block diagram of a system having a user interface for an automated hearing test according to embodiments of the invention.

FIG. 2 illustrates the system 100 in block diagram form. As can be seen, the computer 102 has a number of functional components, including a video unit 200, a central processing unit 202, a hearing test device 204, and a storage unit 206. These components are well known in the computer art and will therefore be described only briefly here. In general, the video unit 200 provides the video signals that are displayed as images on the display screen 104. In some embodiments, the video unit 200 may be any one of several commercially available video cards. The central processing unit 202 is responsible for the overall operation of the computer 102, including execution of the operating system and any software applications residing on the computer 102. In some embodiments, the central processing unit 202 may be any one of several commercially available microprocessors. The hearing test device 204 may comprise any or all of an audiometer, an otoacoustic emission test device, a tympanometer, a masking noise generator, or other hearing test devices. In some embodiments, the hearing test device 204 may be one or more electronic circuit boards within the computer 102 for performing the functionality of such test devices. Alternatively, the hearing test device 204 may be a separate unit that is external to the computer 102. The storage unit 206 provides long-term and temporary (i.e., caching) storage for the software and data that are used by the computer 102 and may include one or more of, for example, a hard drive, main memory, removable storage (e.g., CD-ROM, floppy disk), and the like.

In some embodiments, the storage unit 206 also stores a multimedia user interface 208 for the automated hearing test. More specifically, the storage unit 206 stores a computer-readable version of the user interface 208 that can be executed by the computer 102. During execution, a portion of the user interface 208 may be temporarily loaded from, for example, the hard disk and into the main memory components of the storage unit 206. In addition to the stand-alone arrangement, it is also possible to execute the user interface 208 from a network. For example, the user interface 208 may be stored on a server computer (not expressly shown) that is accessible to several client computers. This arrangement has an advantage in that updates to the user interface 208 may be quickly and easily implemented for all client computers. Other environments for executing the user interface 208 may also be used without departing from the scope of the invention.

Figure 3:
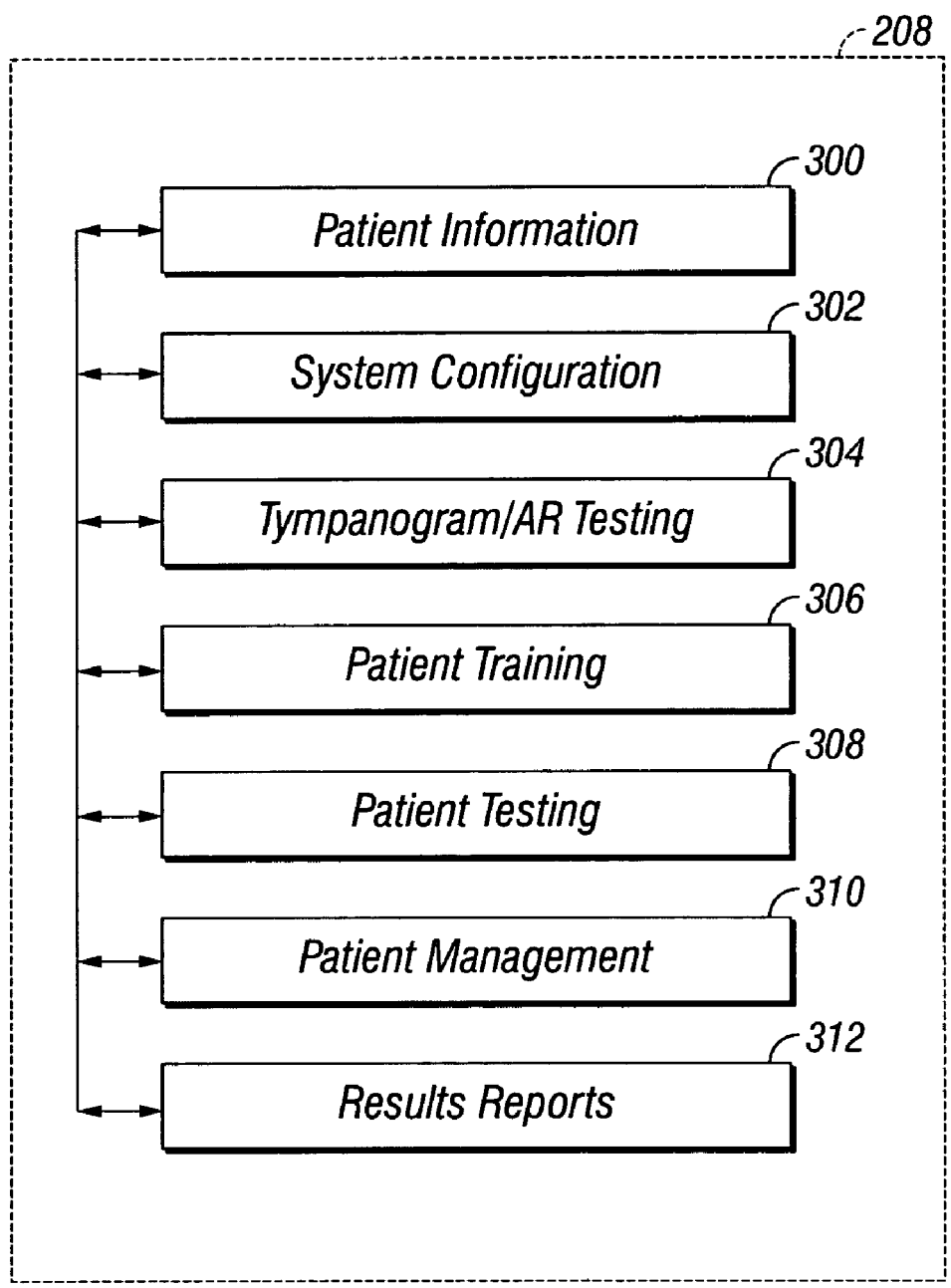
FIG. 3 illustrates an exemplary user interface for an automated hearing test according to embodiments of the invention.

FIG. 3 shows an exemplary implementation of the user interface 208. As can be seen, the user interface 208 has a number of functional components, including a patient input component 300, a system configuration component 302, a tympanogram, acoustic reflex (AR), and otoacoustic emission testing component 304, a patient training component 306, a patient testing component 308, a patient management component 310, and a reporting component 312. The various functional components are typically executed in sequence as the automated hearing test progresses, but any functional component can be executed before, during, or after execution of any other functional component as needed. Operator and/or patient interaction with the user interface 208 may be accomplished using any suitable input device, for example, a mouse, keyboard, separate dedicated response button, or using a touchscreen display unit. Where a touchscreen display unit is used, the user interface 208 may display a graphical keyboard (in addition to or instead of a conventional keyboard) from which the operator and/or patient may select alphanumeric characters as needed.

Briefly, the patient information component 300 allows the operator and/or the patient to enter some basic information about the patient and to select which hearing related tests to perform for the patient. The system configuration component 302 allows the operator to custom configure various aspects of the automated hearing test according to his preference. The tympanogram, acoustic reflex, and otoacoustic emission testing component 304 facilitates obtaining a tympanogram and/or AR test for the patient. The patient training component 306 provides instructions and guides for the patient in the use of the automated hearing test prior to as well as during the actual testing. The patient testing component 308 allows the patient to interact with the automated hearing test based on the particular hearing related tests being performed (e.g., pure tone threshold, speech reception threshold, and speech discrimination). The patient management component 310 notifies the operator and/or the patient of any problems or contingencies that may arise during testing and generally helps the patient stay on course. Finally, the reporting component 312 allows the operator to view and print the results of the testing, as well as to store the results of the testing in various formats. Each of the above functional components will now be described in more detail.

Figure 4:
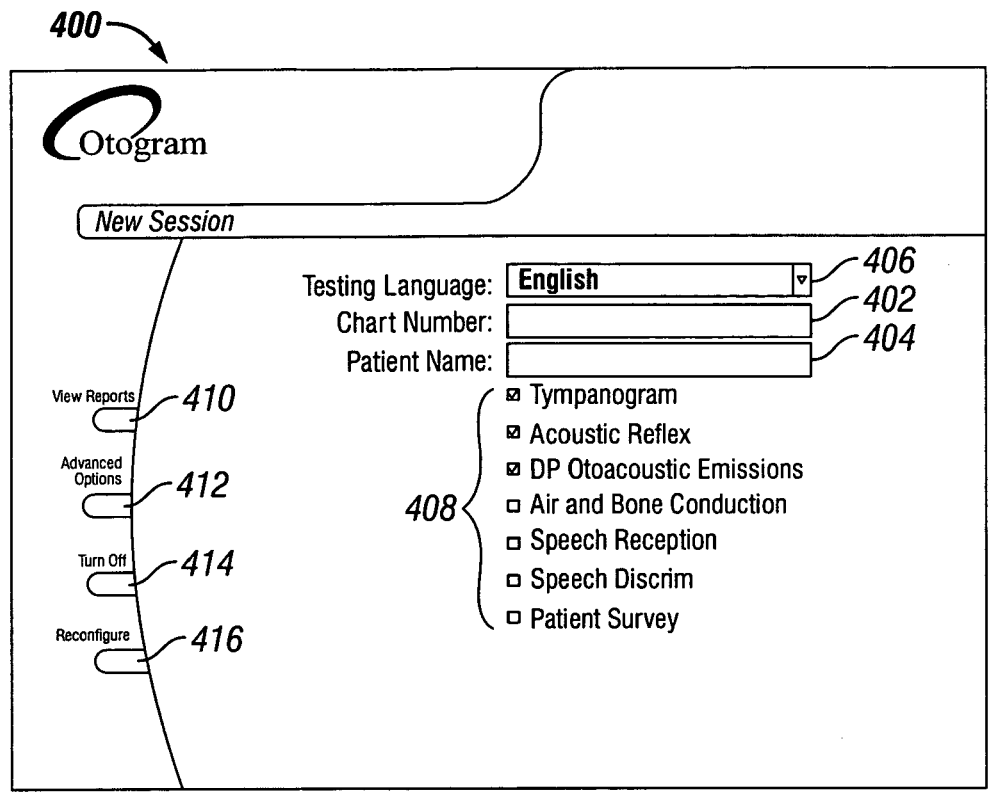
FIG. 4 illustrates an exemplary implementation of a patient input component of the user interface according to embodiments of the invention.
Figure 5A:
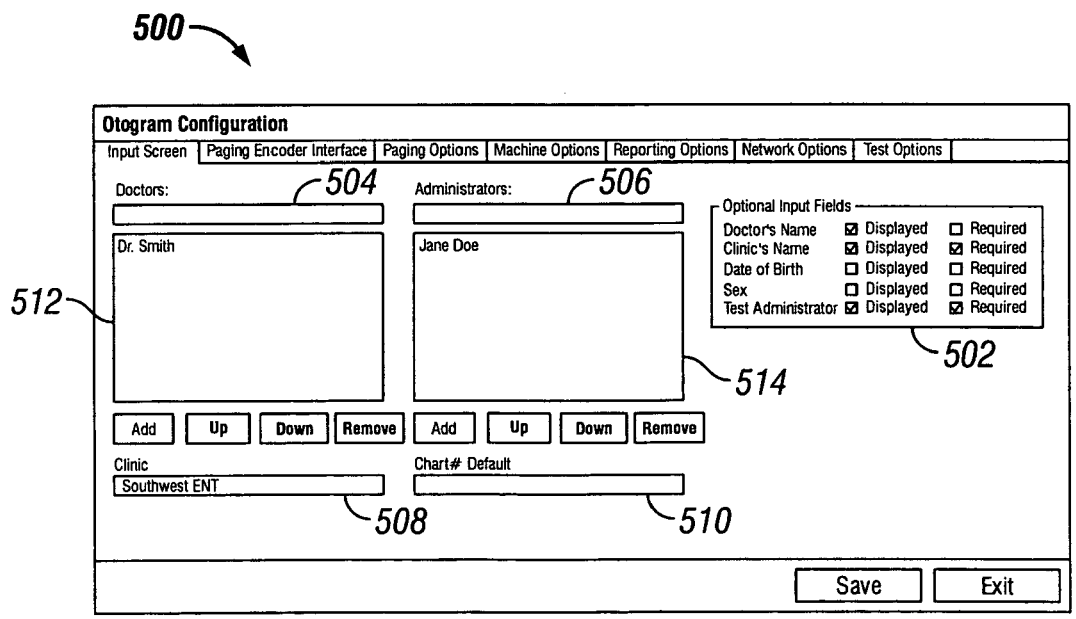

Referring now to FIG. 4, an exemplary implementation of the patient information component 300 is shown. In some embodiments, the patient information component 300 may include a new session screen 400. This is the first screen to be displayed after powering on the system 100 and functions to allow the operator and/or the patient to enter certain items of basic information for the patient. For example, the new session screen 400 may include a chart number field 402 for entering the patient's chart number and a patient name field 404 for entering the patient's name. This information, along with the date and possibly other information, may be used to store and subsequently retrieve the results of any test session. In addition, because the automated hearing test is capable of testing in multiple languages (e.g., English, Spanish, French, etc.), in some embodiments, the new session screen 400 may also include a field 406 for selecting which language to be used to test the patient. The new session screen 400 may also include a plurality of checkboxes 408 for selecting which hearing related tests will be performed for the patient. For example, the new session screen 400 may include a checkbox for selecting a tympanogram test, an acoustic reflex test, and a distortion product (DP) otoacoustic emission test. Also available for selection are an air and bone conduction test, a speech reception test, and a speech discrimination test. Selecting a patient survey allows the automatic hearing test to gather certain hearing related information about the patient that can be used by the hearing health professional to diagnose and recommend treatment.

From the new session screen 400, the operator may access various functions related to the automatic hearing test by pressing the appropriate buttons. For example, pressing a view reports button 410 allows the operator to view patient reports previously stored on the system 100. This aspect of the invention will be described later herein with respect to the reporting component 312. The operator may also press an advanced options button 412 to view and select various advanced options related to a manual testing feature of the automated hearing test that allows the hearing health professional to manually administer the hearing test assisted by the various functions of the automated hearing test (i.e., computer-assisted audiometry). An Off button 414 allows the operator to turn the automated hearing test off. Finally, a reconfiguration button 416 allows the operator to initiate the system configuration component 302 of the user interface 208, described below.

FIGS. 5A-5M illustrate an exemplary implementation of the system configuration component 302 of the user interface 208. In some embodiments, the system configuration component 302 includes a plurality of screens, each screen presenting a different set of system configuration options from which the operator may select. It should be noted that not all screens have to be present in every embodiment, and that additional screens not shown may be present in some embodiments.

In one embodiment, the system configuration component 302 may include an input screen 500. The input screen 500 may have an information selection area 502 that allows the operator to select various items of information to be entered for the patient. The information selection area 502 may include fields for the doctor's name, the clinic's name, the patient's date of birth, the patient's gender, and the name of the operator. The information selection area 502 also allows the operator to choose whether to make certain information items optional only, or required information. Thereafter, at the start of each new test session, the new session screen 400 displays all the fields in the information selection area 502 selected by the operator and then waits for the patient and/or the operator to fill in the fields, either on an optional or a required basis.

In some embodiments, the input screen 500 may also include fields for entering default settings for some of the information items. For example, the input screen 500 may include a default doctor's name field 504, a default administrator's name field 506, a default clinic's name field 508, and a default chart number field 510. In some embodiments, the input screen 500 may further include an area for entering several default doctor's names into a list 512 and several default administrator's names into a list 514. The names that are entered into the lists may then be used as default options in a drop-down list from which the operator and/or the patient may select to fill out the information fields. To add or remove a name from the list, simply click on the appropriate "Add" or "Remove" buttons as needed. To scroll through the list, simply click the "Up" or "Down" navigation buttons as needed.

In some embodiments, the system configuration component 302 further includes a paging encoder interface screen 520. By way of background, the automated hearing test typically includes a patient response system that allows the operator to monitor the patient's progress during the hearing test and also allows patient to contact the operator, usually via a pager, at any time during the test. The function of the paging encoder interface screen 520 is to let the operator customize the paging protocol used by the automated hearing test. To enable paging, for example, a check box 522 may be selected to indicate that a paging device is attached to the automated hearing test. The paging encoder interface screen 520 also makes available a plurality of options 524 for specifying various parameters of the paging encoder interface, such as the communications port, an encoder ID, an encoder timeout period, a pager CapCode, and a pager data rate.

In some embodiments, the system configuration component 302 further includes a paging options screen 530. The paging options screen 530 allows the operator to select when a page will be issued. For example, the paging options screen 530 may include a check box 532 for paging the operator at the end of the test session, a check box 534 for paging the operator at the end of each test in the test session, a check box 536 for paging the operator after a certain amount of inactivity by the patient, and a check box 538 for paging the operator if the automated hearing test cannot determine a pure tone threshold for the patient within a predetermined amount of time.

The paging options screen 530 also includes a plurality of paging options 539 that allows the operator to customize certain aspects of the page. For example, the operator may specify a short text message to be sent with pages that occur at the end of a testing session, and a brief text message to be sent with pages that occur at the end of each test. The operator may also specify a short text message to be sent with pages that occur due to inactivity, and to specify the inactivity threshold. Furthermore, the operator may specify a brief text message to be sent with pages that occur due to the inability to reach a pure tone threshold, and to specify the amount of time to wait for a threshold.

The paging device option 540 allows the operator to specify the type of paging mechanism. For example, the operator may specify a wireless or radio based paging mechanism, a web based paging mechanism wherein an alarm (visual and/or audio) is issued on a web page monitored by the operator, or an FTP based paging mechanism where a file is sent to the operator to notify him of a paging event.

In some embodiments, the system configuration component 302 further includes a machine options screen 544. The function of this screen is to allow the operator to assign a specific identifier to the automated hearing test. This function is especially useful in clinics where multiple systems are used. For example, the machine options screen 544 may include a machine identifier field 546 into which the operator may enter an alphanumeric identifier for the particular automated hearing test.

In some embodiments, the system configuration component 302 further includes a reporting options screen 548. The function of this screen is to allow the operator to pre-configure the number of test reports to be printed automatically after each testing session: For example, the reporting options screen 548 may include a field 550 for entering the number of reports to be printed automatically at the end of a testing session (e.g., 2). In some cases, the reporting options screen 548 also includes a field 552 for entering the minimum testing intensity level that the operator wishes to be reported (e.g., 0 dB).

In some embodiments, the system configuration component 302 further includes a network options screen 554. The function of this screen is to allow the operator to specify where patient reports are stored on a particular computer 102 of the automated hearing test. In the example shown, a field 556 indicates that the patient reports are stored in a directory called "c:\inetpub\wwwroot\" of computer 102. When the computer 102 is accessed from a network, the information that will be available to the network is the patient reports that are stored in the specified directory. Thus, any personnel with authorized access to the network to which the computer 102 is connected may view the patient reports that are stored on the computer 102. In some embodiments, the computer 102 of each automated hearing test functions as a web server, and the field 556 indicates the web server root directory. In that case, the patient reports stored on the computer 102 may be viewed from the network as a web page using any suitable web browser.

In some embodiments, the system configuration component 302 includes a test options screen 560. The function of this screen is to allow the operator to configure various aspects of the hearing related tests that will be performed. For example, the test options screen 560 includes a plurality of checkboxes 562 that allow the operator to specify which hearing related tests will be selected by default from the new sessions screen 400.

The test options screen 560 also includes a plurality of hearing related test option screens, for example, a pure tone options screen 566. Because naming conventions for the various hearing related tests differ from country to country, the pure tone test options screen 566 includes a naming field 568 to allow the operator to customize the test name used for this test in his clinic. The pure tone test options screen 566 further includes frequency options 570 that allow an operator to specify when the various pure tone frequencies are tested. For example, the operator may specify that a certain frequency is always tested, never tested, or tested as needed. The operator may define the pure tone average (PTA) for the pure tone test by selecting one of several predetermined definitions at 572. A check box 574 allows the operator to always use bone masking if he so desires.

In some embodiments, another hearing related test options screen that is included is the tympanometry options screen 576. This tympanometry options screen 576 allows the operator to specify various parameters for the tympanometry test. For example, the tympanometry options screen 576 includes field 578 where the operator may specify a name for the test, the communications port, and may select one of several available to manometer. The tympanometry options screen 576 also includes field 580 for allowing the operator to specify the starting pressure and the ending pressure for the test. A plurality of calibration parameters 582 allows the operator to enter calibration values for the left and right ear and to calibrate the tympanometer for those ears accordingly.

In some embodiments, the test options screen 560 further includes an acoustic reflex options screen 583 that can be used to specify various parameters for the acoustic reflex test. For example, the acoustic reflex options screen 583 may include a field 584 that allows the operator to specify the name to be used with the test. Checkboxes 585 allow the operator to specify which one of several available frequencies to be used with the ipsilateral and contralateral ear. The initial intensity level, incremental intensity, and the reflex threshold level may also be specified in the fields shown at 586.

In some embodiments, yet another hearing related test options screen that is included is the speech discrimination options screen 587. This screen allows the operator to specify various parameters for the speech discrimination test, including the name of the test at 588. A plurality of fields 589 allow the operator to specify, for example, the base presentation level, the presentation type (e.g. closed, open), the number of presentations, the minimum presentation level, the maximum presentation level, and the particular word list to be used.

In some environments, the test options screen 560 additionally includes a speech reception threshold options screen 590 that can be used to specify various parameters for the speech reception threshold test. For example, the speech reception threshold options screen 590 may include a field 591 for specifying the name to be used for the test.

In embodiments where a patient survey is taken, the test options screen 560 may include a survey options screen 592. This screen can be used to specify various aspects of the survey at 593, including the name to be used for the survey, and the particular survey of several available surveys to be used.

Finally, in some embodiments, the test options screen may include an otoacoustic emission options screen 594. The otoacoustic-options screen 594 may include a naming field 595 for specifying the name to be used with this test. A set of options 596 allows the operator to select which one of several frequencies to test, set the response floor and noise ceiling, and specify the intensity levels L1 and L2.

Figure 6A:
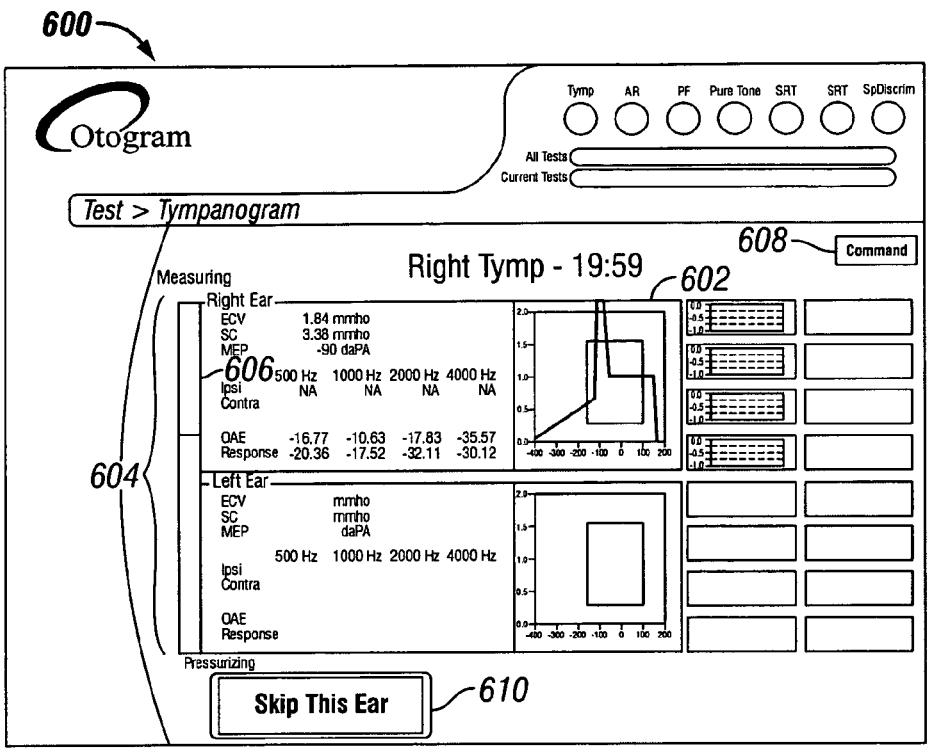
FIGS. 6A-6B illustrate an exemplary implementation of a tympanometry, acoustic reflex, and otoacoustic emission component of the user interface according to embodiments of the invention.
Figure 6B:
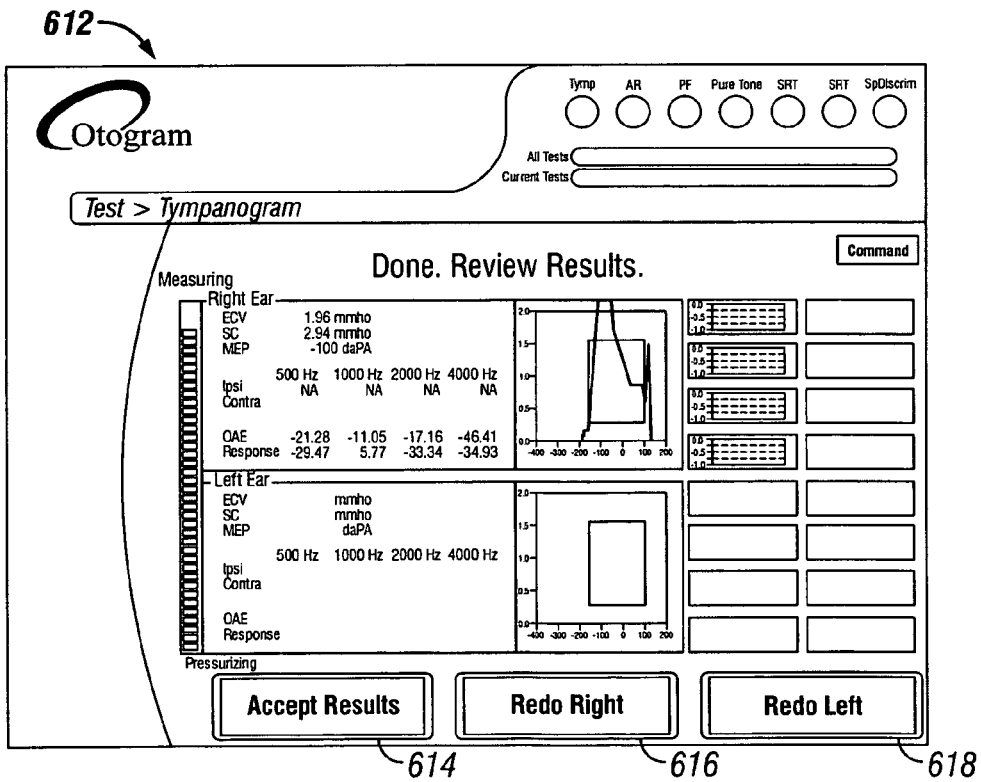

FIGS. 6A-6B illustrate an exemplary implementation of the tympanometry, acoustic reflex, and otoacoustic emission component 304 of the user interface 208. In some embodiments, the tympanogram, acoustic reflex, and otoacoustic emission component 304 includes a combination test screen 600. The function of this screen is to allow the operator and/or the patient to obtain a tympanogram, acoustic reflex, and otoacoustic emission measurement for the patient. Note that although all three tests may be performed from the same screen, only the tests that have been selected will be performed. The tympanogram, acoustic reflex, and otoacoustic emission screen 600 may include a series of instructions for the operator and/or patient that walks him step-by-step through the procedure. The instructions may be presented in text, or they may be presented verbally, or both. Where verbal instructions are presented, a confirmation button (not expressly shown) may be pressed to confirm completion of each instruction and move on to the next instruction. While the test is being performed, the screen 600 includes a chart 602 that captures the data being obtained for the tympanogram. The raw data is shown generally at 604. The amount of pressure that is being used is shown at 606. Pressing a command button 608 brings up a list of commands that may be selected (e.g., exit, pause, microphone on, etc.). Pressing a skip button 610 allows the operator and/or the patient to skip the current ear and move to the next ear.

When the tympanogram, acoustic reflex, and otoacoustic emission portion is completed, a screen 612 presents the final results. From this screen, the operator and/or patient may press an accept results button 614 to accept the results, a redo right ear button 616 to redo the right ear, and a redo left ear button 618 to redo the left ear.

Once the tympanogram, acoustic reflex, and otoacoustic emission portion is completed and the results therefor accepted, the patient may proceed with the remaining hearing related tests. First, however, the patient should be given some instructions and guidance on how to proceed and what to expect. The patient training component 306 performs this training task. Patient training is given in two phases, a general training phase where general instructions are given, and a test specific phase where instructions that are specific to a particular test are given before the test begins.

Figure 7A:
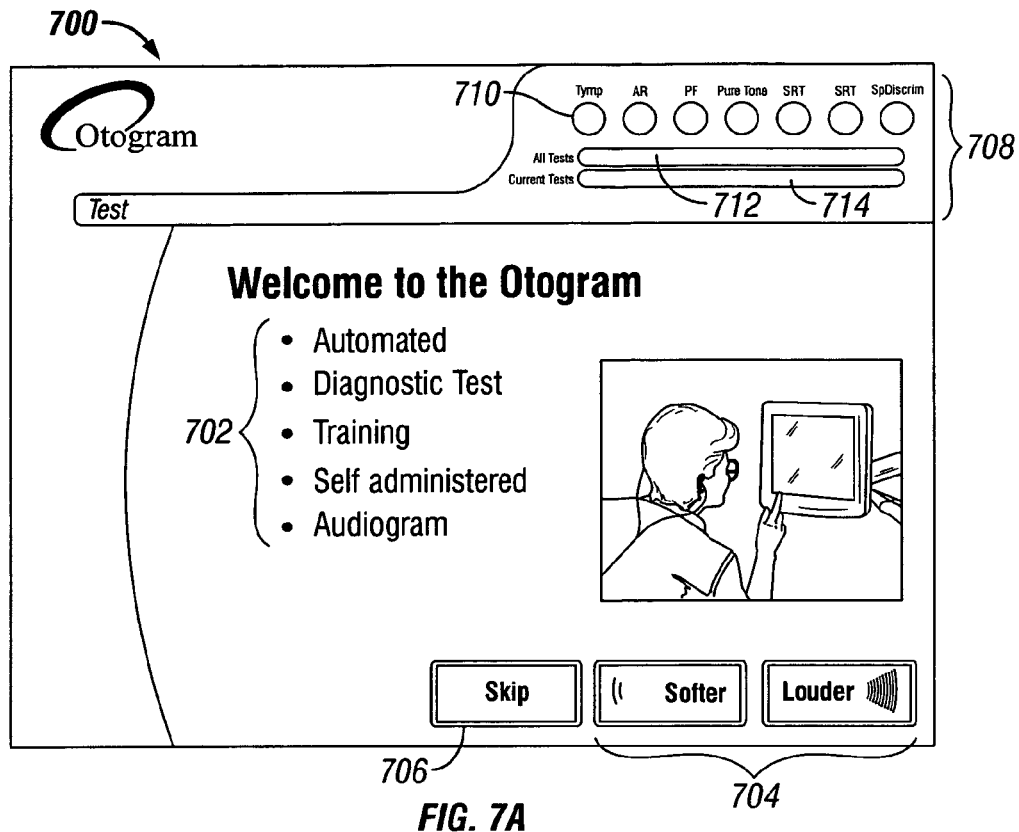
FIGS. 7A-7B illustrate an exemplary implementation of a portion of a patient training component of the user interface according to embodiments of the invention.
Figure 7B:
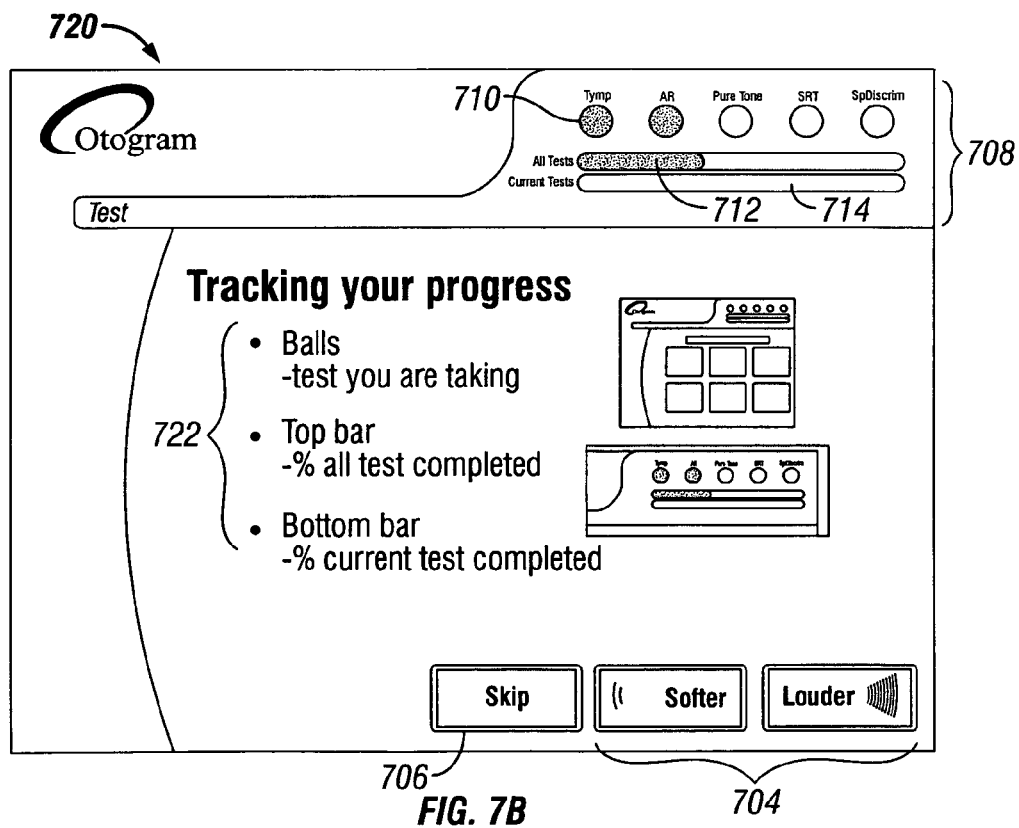
Figure 8A:
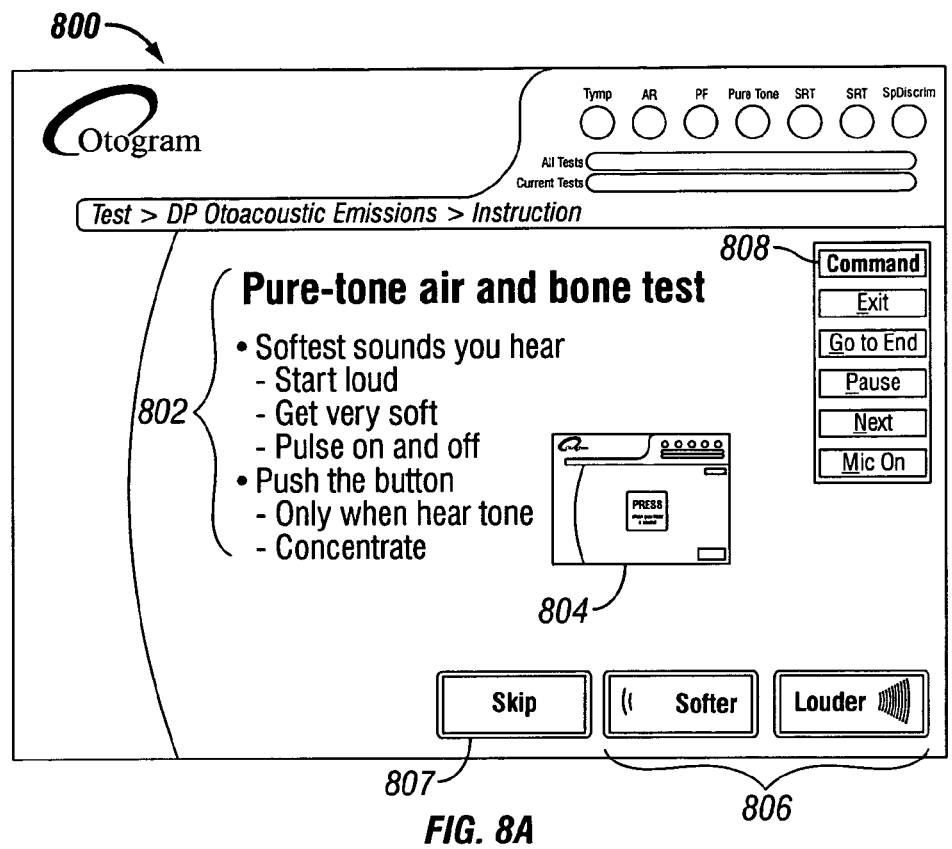
FIGS. 8A-8I illustrate an exemplary implementation of a patient testing component of the user interface according to embodiments of the invention.
Figure 8B:
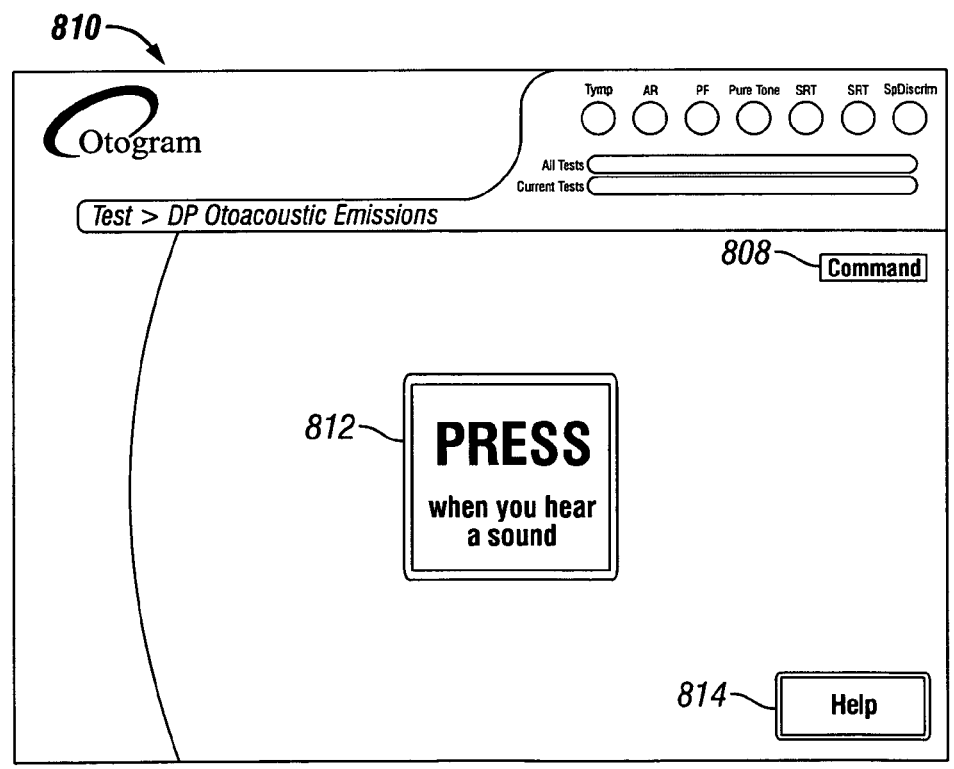
Figure 8C:
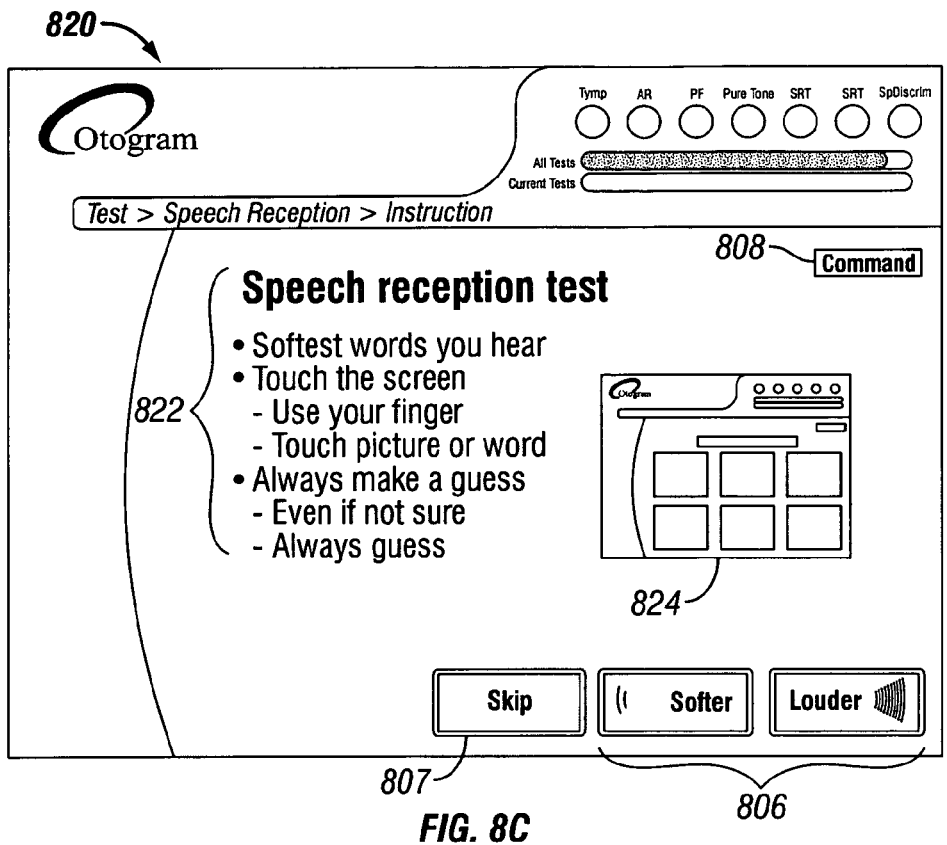
Figure 8D:
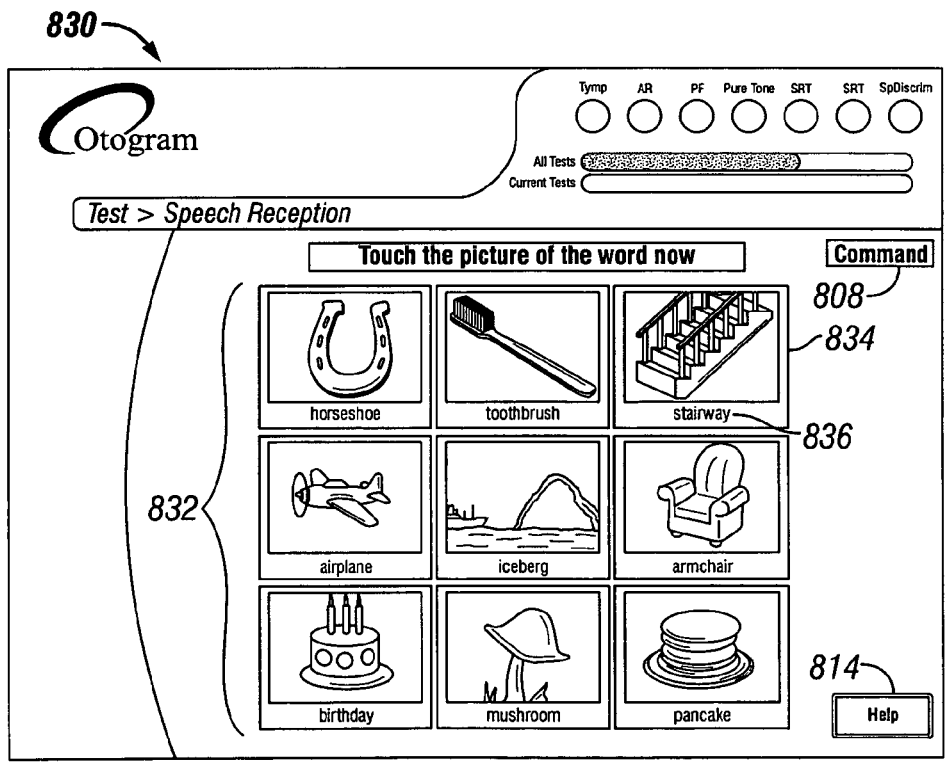
Figure 8E:
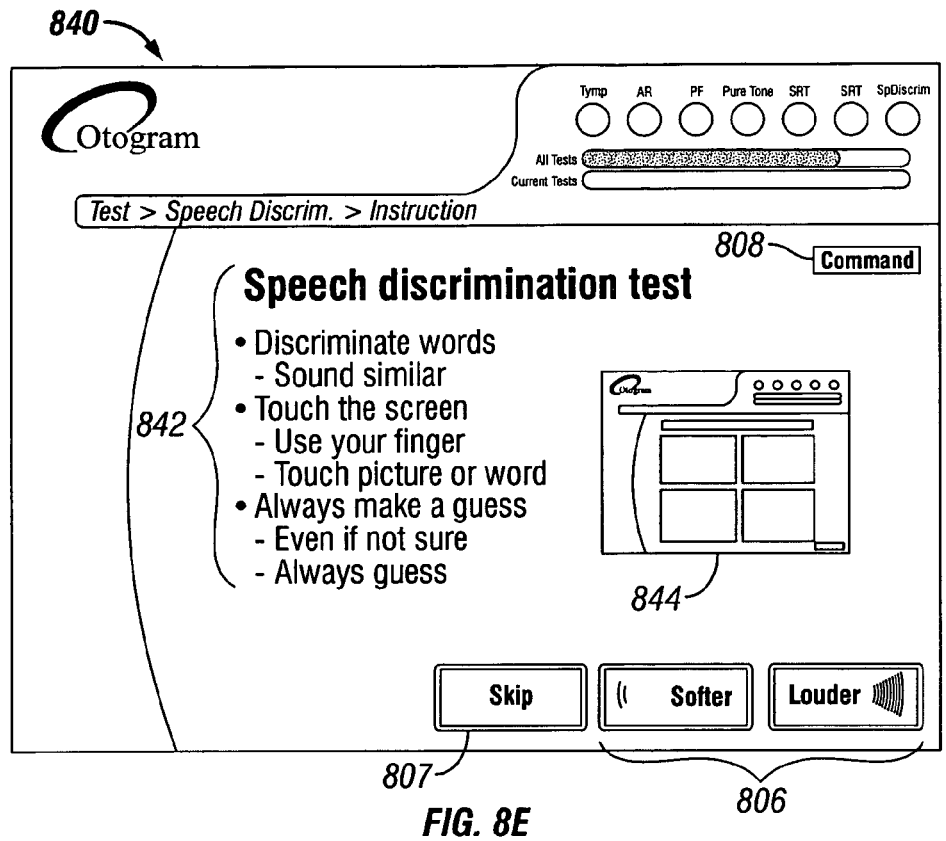
Figure 8F:
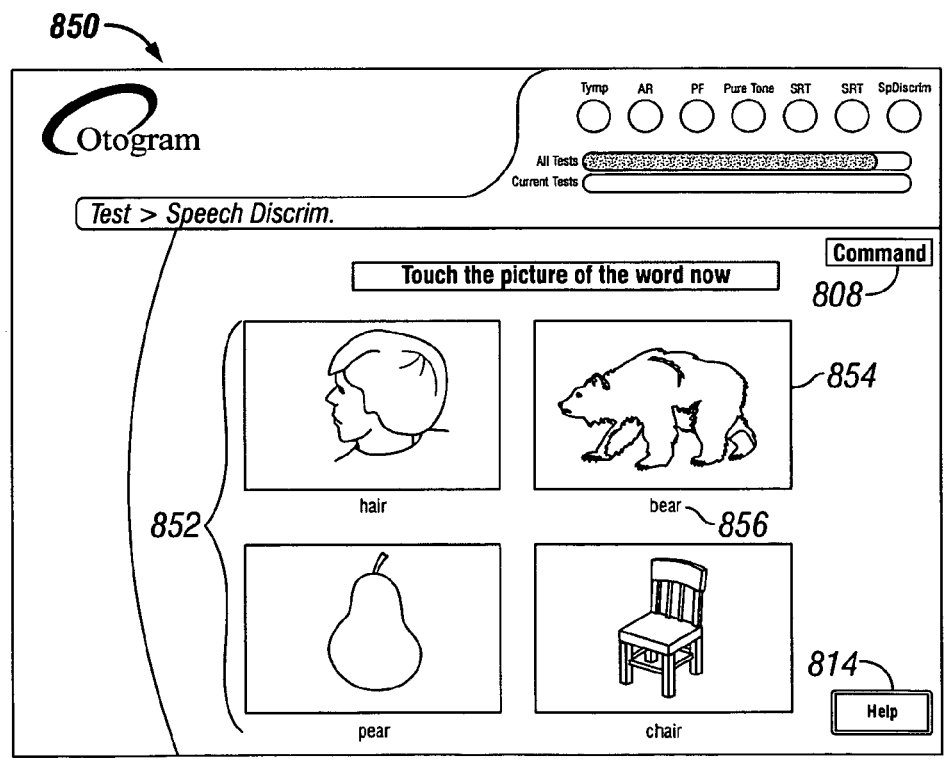
Figure 8G:
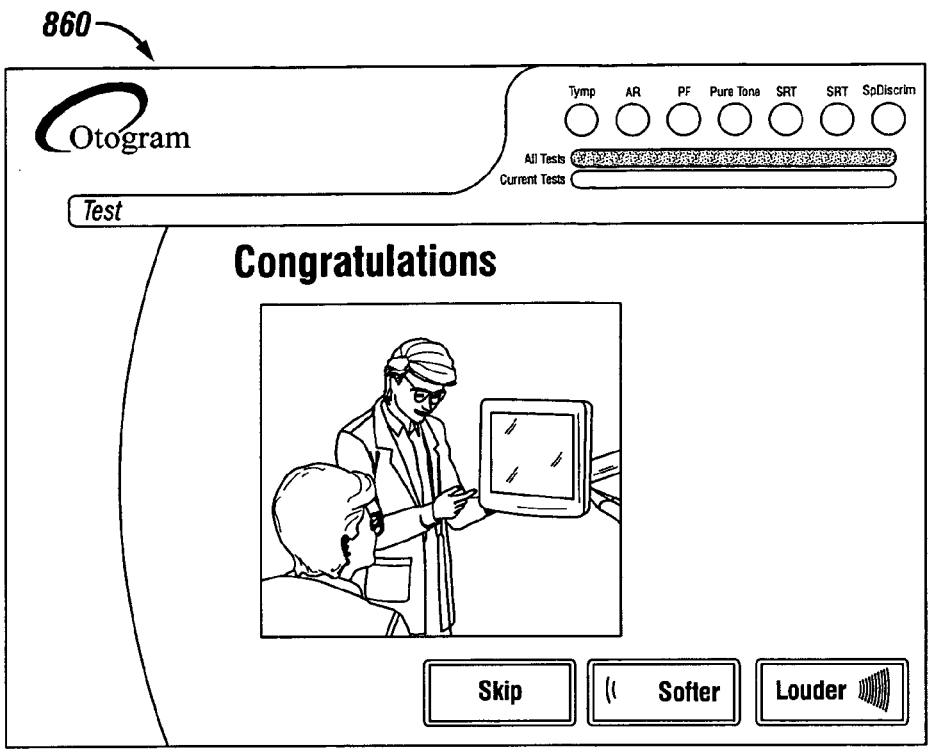
Figure 8H:
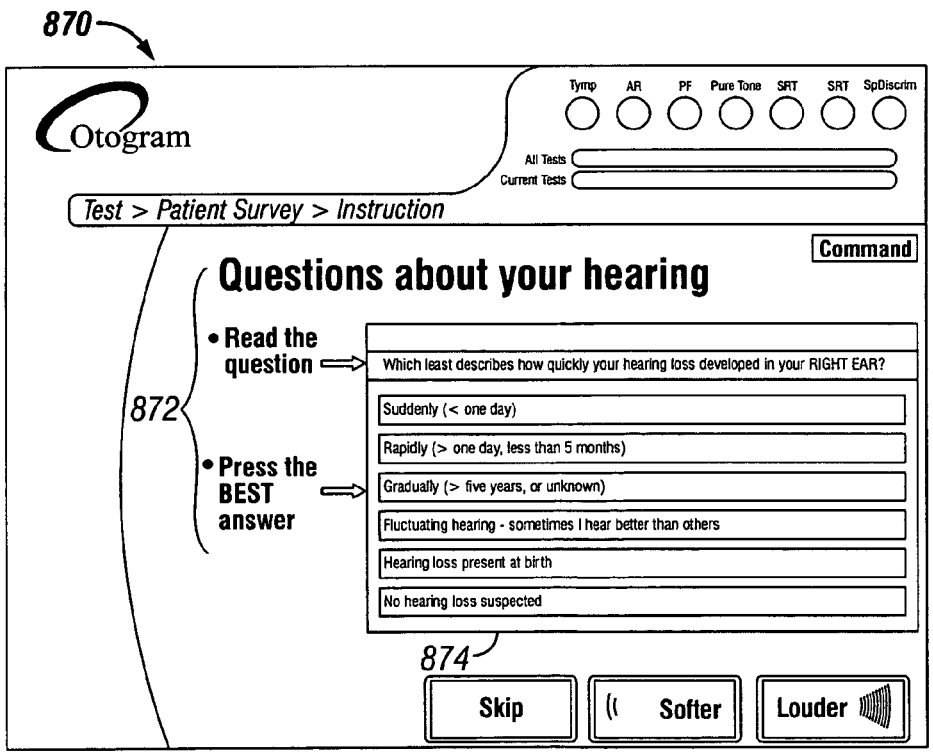
Figure 8I:
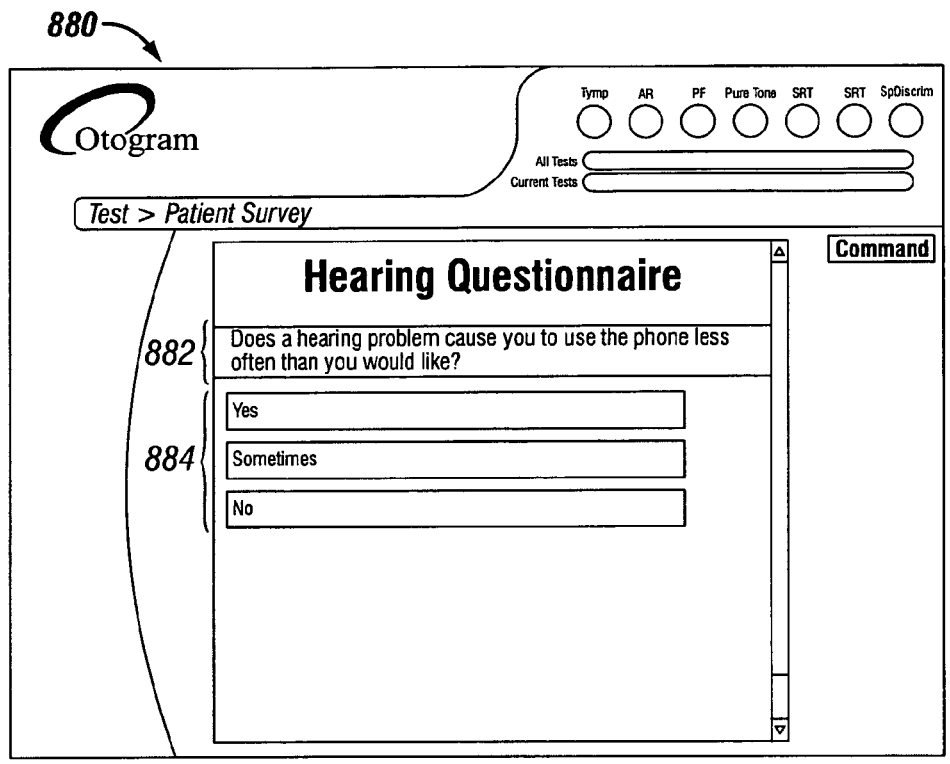

FIGS. 7A-7B illustrate an exemplary implementation of the general phase of the patient training component 306. In some embodiments, the general training phase includes a welcome screen 700. The function of this screen is to give the patient a general idea of how the automated hearing test works in general. For example, the welcome screen 700 may display some of the basic instructions (shown generally at 702) for the automated hearing test. At the same time, the patient training component 306 may cause a verbal welcome message to be played in the transducers worn by the patient. The welcome message my provide the patient with detailed information about the upcoming tests. For example, the welcome message may explain that the tests are automated and therefore the operator may not be in the room during the test, but that the patient may press the help button at any time to call the operator. Volume control buttons 704 allow the patient to increase or decrease the volume of the welcome message as needed. If the patient wishes to skip the message altogether, he may press the skip button 706.

Before discussing the patient training component 306 further, it may be useful to discuss one aspect of the patient management component 310 of the user interface 208. In some embodiments, the patient management component 310 may include a progress indicator 708 that allows the patient and/or operator to track the patient's progress for a given test session. The progress indicator 708 may include a plurality of bubbles, one of which is shown at 710, to indicate the patient's current hearing related test. For example, there is a bubble for the tympanometry test, the acoustic reflex test, the otoacoustic emission test, the pure tone threshold test, the speech reception test, and the speech discrimination test. The bubbles are empty at first, but as the patient begins a particular hearing related test, the bubble for that test is filled in. The color used to fill in the bubbles may be the same for every bubble, or some type of progressive color scheme may be used (e.g., darker colors at the beginning stages and brighter colors at the end).

In some embodiments, the progress indicator 708 of the patient management component 310 may also include progress bars 712 and 714. The progress bars 712 and 714 provide an indication of the completion percentage of the total test session and of each individual hearing related test, respectively.

Continuing now with the general training phase of the patient training component 306, if a progress indicator 708 is present, the patient training component 306 also provides training on how the patient can track the progress of his testing using the progress indicator 708. For example, after the welcome message is completed (or skipped), the patient training component 306 may present a progress training screen 720. The progress training screen 720 may display a text explanation 722 of the basic feature of the progress indicator 708. In addition, or alternatively, a detailed verbal explanation of the progress indicator 708 may also be presented. Both the text and verbal based training explain to the patient how to interpret the plurality of bubbles 710 and the progress bars 712 and 714.

After the general training stage is completed, the patient training component 306 then provides the test specific training. The test specific training may be provided for the specific tests that are about to be performed only, or it may be provided for all the available hearing related tests. In addition, the test specific training may be provided all at once and upfront before beginning any specific test, or the training for a specific test may be provided one test at a time before beginning that hearing related test. This latter embodiment will now be explained in conjunction with an explanation of the patient testing component 308.

In general, at the beginning of each test, the patient training component 306 presents the patient with an instruction screen and/or a verbal explanation of the test. The instruction screen may show some of the basic instructions for the test and how to proceed, and the verbal explanation may provide a more detailed explanation. The patient testing component 308 then allows the patient to proceed with the actual testing. FIGS. 8A-8I illustrate an exemplary implementation of the patient testing component 308 and the test specific training portion of the patient training component 306.

For example, where the patient is getting ready to take the pure tone threshold portion of the automated hearing test, the patient training component 306 presents the patient with a pure tone threshold training screen 800 and, in some cases, a verbal explanation thereof The pure tone threshold training screen 800 includes text 802 that list some of the basic instructions for the pure tone threshold test, for example, that the tones start loud, then get soft, then pulse on and off. The training screen 800 may also present an example 804 of the response button with an explanation that the patient is to push the button only when he hears a tone. The verbal explanation, when used, may provide essentially the same information plus a few more details, such as the fact that one ear will be tested at a time, and may also provide a sample tone. Volume control buttons 806 allow the patient to control the volume of the verbal message, and a skip button 807 allows the patient to skip the verbal message. A command button 808 brings up a list of commands that may be used at this point.

After the pure tone threshold training is completed, the patient testing component 308 presents the patient with a response screen 810 for responding to the pure tone threshold test. The purpose of the pure tone threshold test is to determine the patient's hearing threshold (i.e., the softest level he can hear) at various frequencies or tones. To this end, the response screen 810 may include a button 812 that the patient can press each time he hears a tone. Where color is used, the button 812 and the screen 810 may have a comfortable yet distinctive color scheme that helps the patient to concentrate on the test. For example, the button may be vivid color such as red, while the surrounding area may have a lighter, softer color. Other suitable color schemes may also be used here as well as throughout the various drawings. In addition, or alternatively, the patient testing component 308 may activate or engage a separate response button (not expressly shown) that the patient may press each time he hears a tone. The automated hearing test then presents a series of tones to the patient, and the patient testing component 308 waits for the patient to respond by pressing the button 812. A help button 814 allows the patient to call the operator at any time.

Where the patient is to undergo a speech reception threshold portion of the automated hearing test, the patient training component 306 presents the patient with a speech reception training screen 820 and, in some cases, a verbal explanation thereof The speech reception training screen 820 includes some of the basic instructions 822 for the test, for example, that there will be X pictures, and that the patient should always make a guess at the correct answer, even if he is not sure. In addition, the speech reception training screen 820 may also include an example 824 of the test screen displayed during the test. The verbal explanation, when used, may provide essentially the same information plus a few more details, such as how many pictures will be shown to the patient.

After the speech reception training is completed, the patient testing component 308 presents the patient with a response screen 830 for responding to the speech reception threshold portion of the automated hearing test. The speech reception threshold test is used to determine the softest level at which the patient can hear and recognize a word. To this end, the response screen 830 presents a set 832 of randomly chosen pictures (one shown at 834) to the patient along with the corresponding words (one shown 836) for the pictures. In some embodiments, there are nine randomly chosen pictures and words in a set 832, and the same set 832 is used for the entire speech reception threshold portion, although it is possible to use more than one set. Preferably, the words that are used are compound words with two distinct syllables. For languages where no such words are used, appropriate substitutes may be made. The automated hearing test then verbally presents the words to the patient one at a time, randomly, and at decreasing intensity level, with no emphasis on any syllable. The patient testing component 308 then waits for the patient to select the picture or word from the response screen 830 that matches the verbally presented word. This procedure is performed for each ear until the lowest or softest verbal presentation level at which the patient can correctly identify 50% of words is determined.

Where the patient is to undergo the speech discrimination portion of the automated hearing test, the patient training component 306 presents the patient with a speech discrimination training screen 840 and, in some cases, a verbal explanation thereof The speech discrimination training screen 840 includes some of the basic instructions 842 for the test, for example, that there will be X pictures, and that the patient should always make a guess at the correct answer, even if he is not sure. In addition, the speech discrimination training screen 840 may also include an example 844 of the test screen displayed during the test. The verbal explanation, when used, may provide essentially the same information plus a few more details, such as how many pictures will be shown to the patient.

After the speech discrimination training is completed, the patient testing component 308 presents the patient with a response screen 850 for responding to the speech discrimination portion of the automated test. The speech discrimination test, unlike the pure tone threshold and speech reception threshold tests, does not test for the softest level the patient can hear. Rather, the speech discrimination test checks to see how well the patient is able to discern between similar sounding words. To this end, the response screen 850 presents randomly chosen sets 852 of pictures (one shown at 854) along with their corresponding words (one shown at 856). The words 856 are preferably single syllable words that sound alike. In some embodiments, there are four such words 856 along with their corresponding pictures 854 in each set 852. For languages where such words are not available, appropriate adjustments may be made.

As each set 852 of pictures is presented on the response screen 850, the automated hearing test verbally presents one of the words 856 to the patient, preferably at a constant level. The level at which the word is verbally presented is chosen so that the patient is mostly like to correctly hear the word presented. Usually the same word from each set 852 is verbally presented. It is possible for some sets 852 to have overlapping pictures, but the same set 852 of pictures should not be repeated. The automated hearing test randomly chooses the sets 852 of pictures from a large pool of such sets, then presents one word from each set at a constant level. The patient testing component 308 thereafter waits for the patient to select the picture or word from the response screen 850 that matches the verbally presented word. The automated hearing test continues this procedure until either a sufficient percentage of correct responses has been received (e.g., 85 percent), or a large enough sample has been obtained to give an accurate assessment.

In some embodiments, the patient management component 310 includes a congratulatory screen 860 that is used to notify the patient and congratulate him for successfully completing the hearing related tests. In some cases, the congratulatory screen 860 may also be accompanied by a verbal congratulatory message informing the patient that he has completed the tests and, if appropriate, the patient will now be given instructions for a survey.

An example of a survey instructions screen is shown at 870. The purpose of the survey instructions screen 870 is to instruct the patient regarding how to take the survey. Thus, the survey instruction screen 870 may include a set of instructions 872 that tells the patient, for example, that he should read the questions and then select the best answer. An example of the survey is given at 874. In some embodiments, a verbal message may also be presented that explains the survey in more detail. For example, the verbal message may explain that the purpose of the survey is to gather information about the patient to help the hearing health professional provide a diagnosis and recommend treatment, if necessary.

Once the instructions are completed, the patient is presented with a survey screen 880. The survey screen includes a survey question 882 followed by a set of answers 884. After the patient reads the question, he may then select the best answer from the set of answers 884. This process is continued until all the survey questions have been answered.

Figure 9:
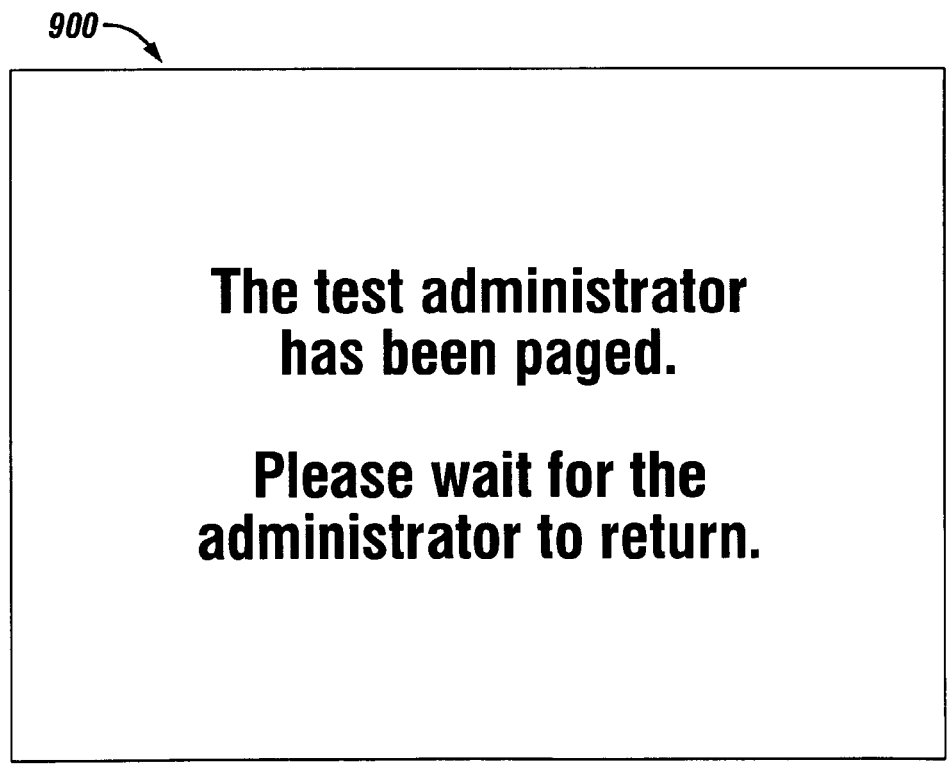
FIG. 9 illustrates an exemplary implementation of a patient management component of the user interface according to embodiments of the invention.
Figure 10A:
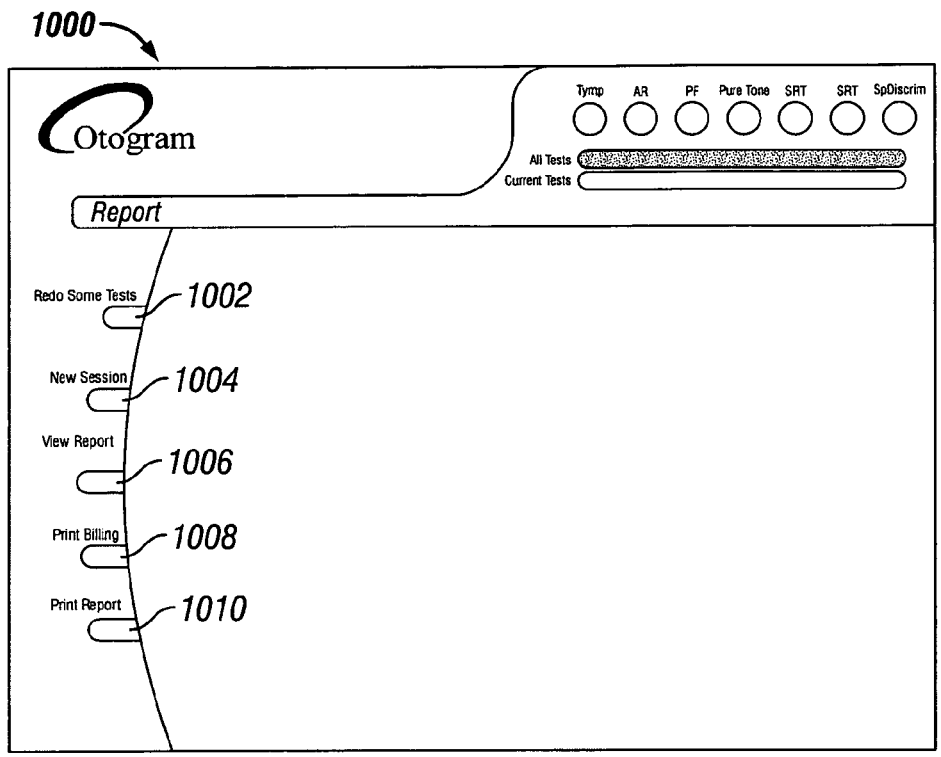
FIGS. 10A-10F illustrate an exemplary implementation of a reporting component of the user interface according to embodiments of the invention.
Figure 10B:
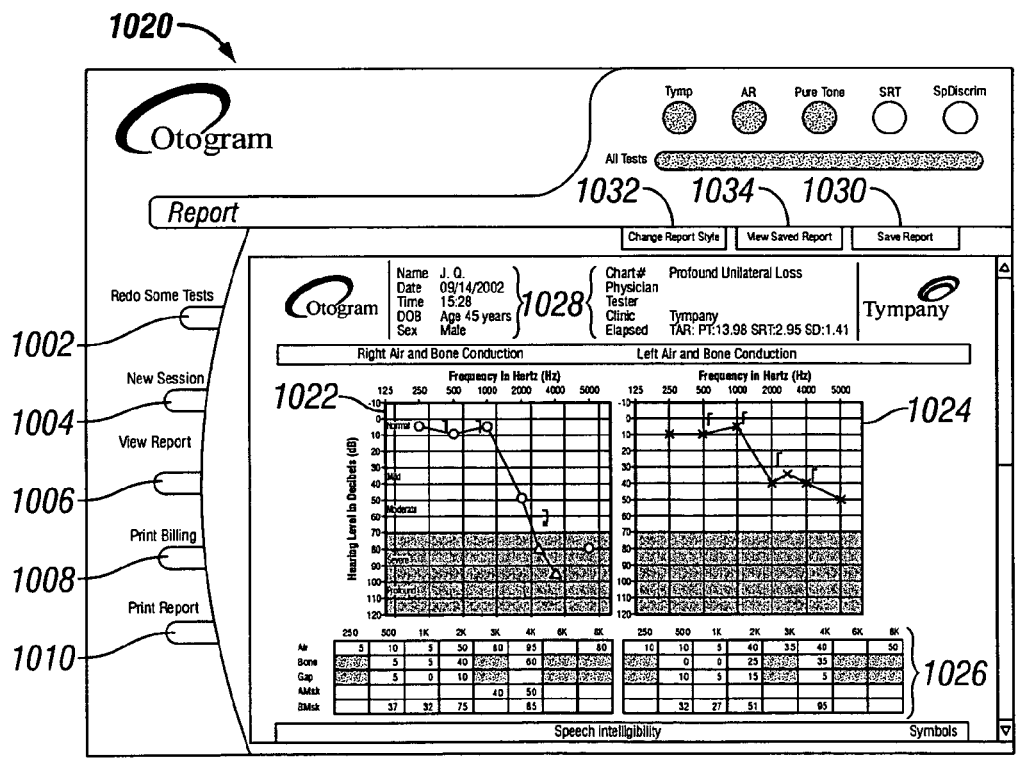
Figure 10C:
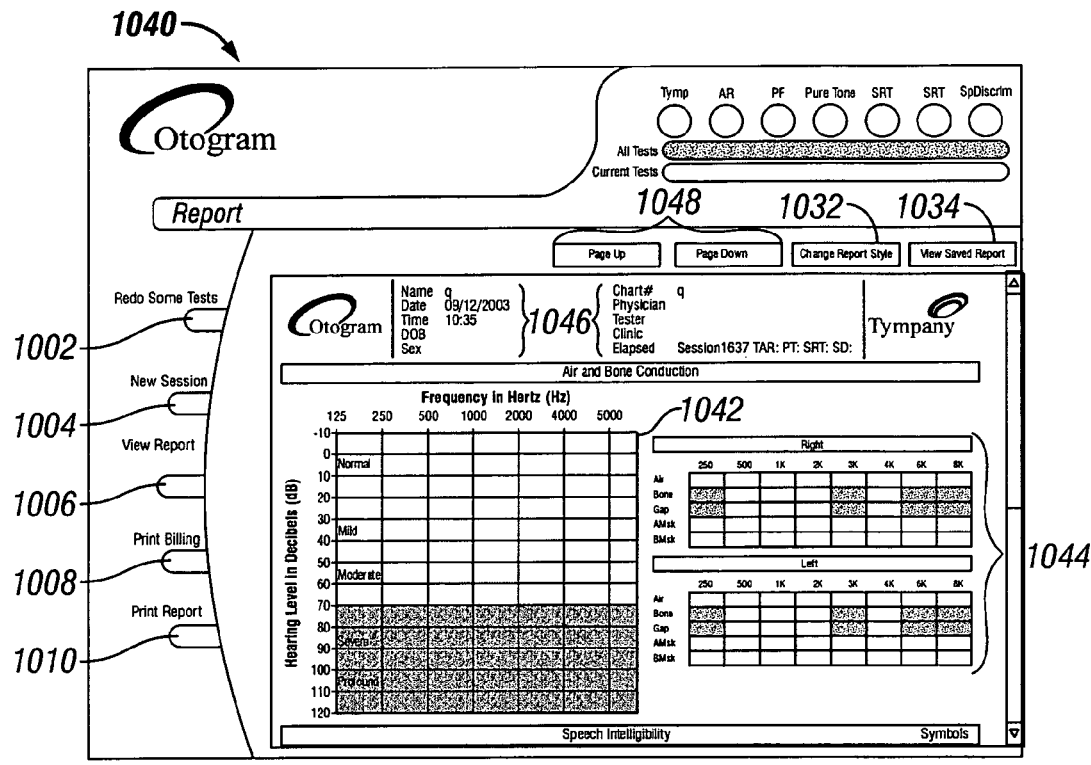
Figure 10D:
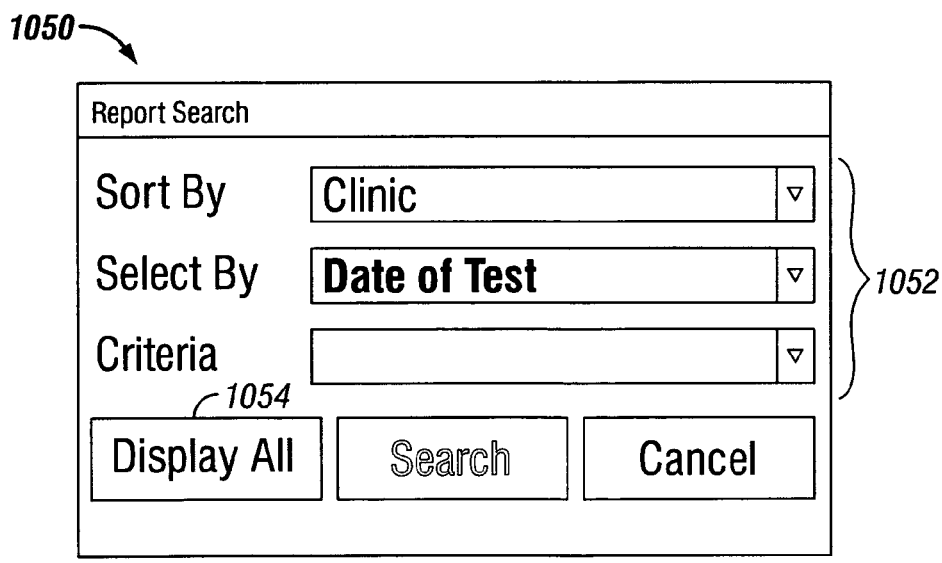
Figure 10E:
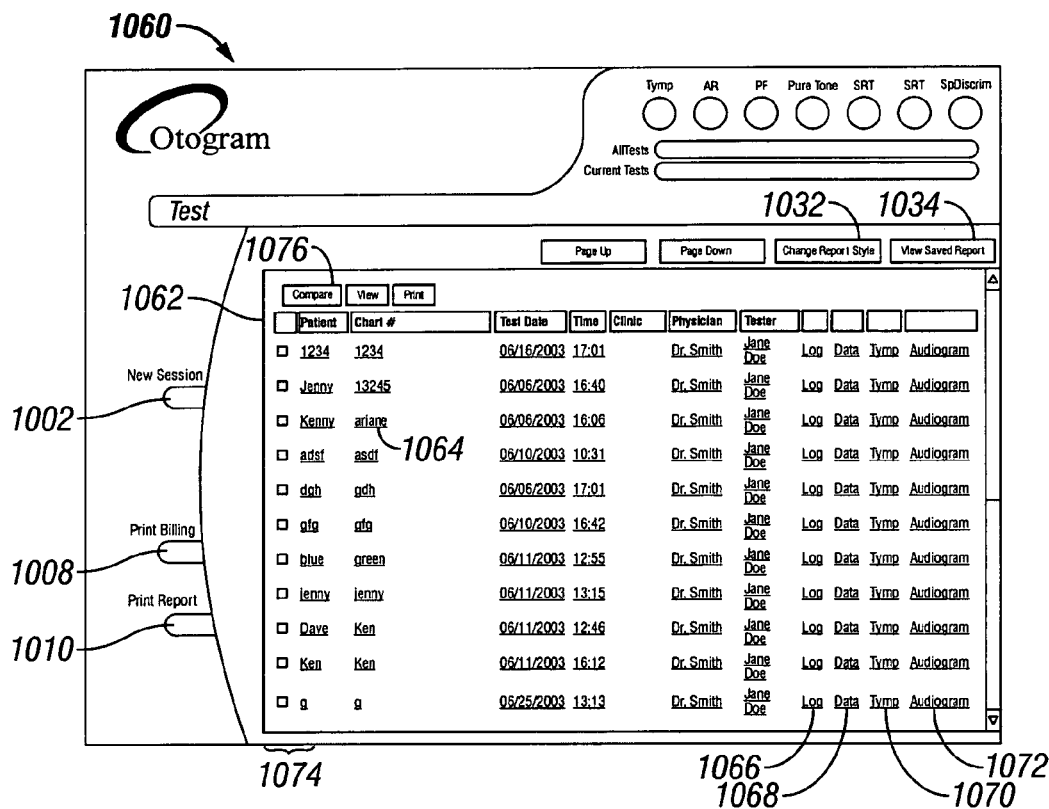
Figure 10F:
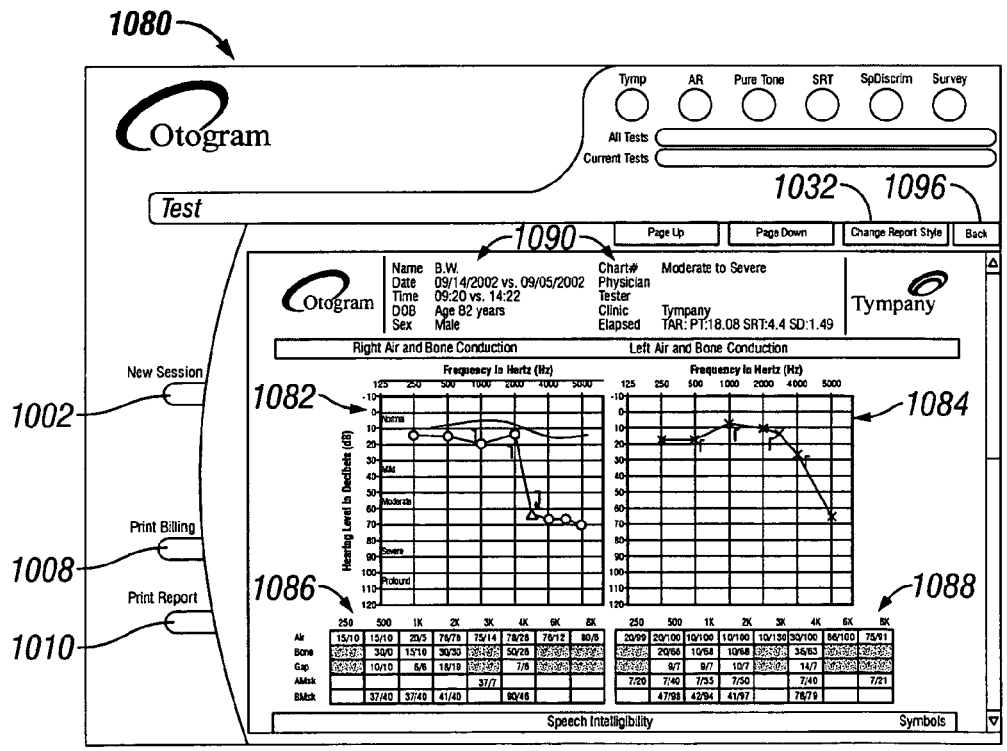

FIG. 9 illustrates an exemplary implementation of the patient management component 310. As mentioned above, the function of the patient management component 310 is to notify the operator and/or patient of any problems or contingencies that may arise, and to generally help the patient stay on course through the testing. For example, if the patient is not responding during a test, or is responding too quickly, the patient management component 310 may issue an on-screen warning to the patient. The warning may include a short text message describing the problem to the patient, and may include an on-screen acknowledgment such as an "Okay" button or a "Continue" button. The patient must then acknowledge the warning by pressing the acknowledgement button in order to continue testing. A verbal warning may also accompany the on-screen warning.

If the patient's responses indicate that there is an equipment problem or some other problem that requires the operator's attention, the automated hearing test may alert the operator. Alerting the operator may be accomplished by wireless paging or by any other suitable techniques (e.g., e-mail, console lights, buzzer, etc.). In the event that the operator needs to be paged, the patient management component 310 includes a paging screen 900 that can be used to inform the patient that the operator is being paged. For example, the paging screen 900 may include a short text message saying that the operator is being paged and that the patient should simply wait for the operator to come in.

FIGS. 10A-10F illustrate an exemplary implementation of the reporting component 312 of the user interface 208. The reporting component 312 allows the operator to view the results of the hearing test, and to save them in various formats (e.g., xml, html, etc.). In some embodiments, the reporting component 312 includes a reporting screen 1000 from which the operator may select a number of options. For example, the operator may press the redo some test button 1002 to redo one or more hearing related tests. Selecting this button returns the operator to the new session screen 400, but the patient's basic information is retained so that one or more tests may be performed again without having to re-enter the basic information. Pressing the new session button 1004 returns the operator to the new session screen 400, but clears the basic information fields so that new information may be entered.

Pressing the view reports button 1006 allows the operator to search and view the results of previous hearing tests saved on the system 100. Pressing the print billing button 1008 prints the billing information associated with the patient, including insurance codes for services rendered. Pressing the print report button 1010 prints a one-page report that contains all the relevant results of the patient's hearing test that a physician usually would like to see.

An example of a report that is generated when the view report 1006 button is pressed can be seen from the report screen 1020. The report screen 1020 may present the results of the hearing test in a two-panel format, with the results of the right ear in one chart 1022, and the results of the left ear in another chart 1024. The charts 1022 and 1024 are computer-generated audiograms that reflect the patient's performance for a particular test (e.g., the air and bone conduction test). Other charts are available for other tests within a specific test session, as well as charts from multiple test sessions for a particular patient. The relevant data for each chart is also displayed (generally at 1026), as well as some basic information (generally at 1028), including the patient's name, date and time of the test, chart number, the physician, the tester, the clinic, and the elapsed time for the test.

A save report button 1030 allows the operator to save the results of the current hearing test. Pressing this button brings up a save report dialog box (not expressly shown) that allows the operator to specify a name for the report and to save the report under that name.

A change report style button 1032 allows the operator to change the style of the report from the two-panel format to, for example, a one-panel format 1040, where data for both ears are presented in one chart. As can be seen, the one-panel format 1040 includes a single chart 1042 along with the data therefore (generally at 1044). Basic information 1046 about the patient is also provided. Navigation buttons 1048 allows the operator to navigate around the report.

A view saved report button 1034 allows the operator to view reports that have been previously saved. Note that this task can also be performed by pressing the view reports button 410 from the new sessions screen 400 in FIG. 4. Pressing either button brings up a search screen 1050, from which the operator may search for previously saved reports to open and view. The search screen 1050 includes a plurality of search criteria 1052 that the operator can use to find previously saved reports. Pressing the search button initiates the search. Pressing the display all button 1054 results in all of the previously saved reports being displayed.

The reporting component 312 also includes a search result screen 1060 that presents the results of the search. This screen lists all the available reports 1062 that match the one or more search parameters from the report search dialog box 1050. The reports are listed in this example according to the date they were taken, but they may certainly be listed in some other order if desired. In addition to the date information, other information about the reports may also be shown, such as the patient name, the chart number, the test time, the clinic, the physician overseeing the test, and the operator administering the test. In some embodiments, each patient's name and chart number is a hyperlink 1064 that takes the operator to the report associated with that patient's name or chart number. As mentioned previously, in some embodiments, each report can be viewed as a web page using any suitable web browser.

The result screen also includes a log hyperlink 1066 that allows the operator to view a log for any report. The log includes a listing of every action taken by the patient and/or operator (e.g., picked the wrong picture for word) during the test as well as every action taken by the automated hearing test (e.g., increased intensity at 5 kHz by one increment). A data hyperlink 1068 to the data allows the operator to view the raw data for any test session. A tympanogram hyperlink 1070 allows the operator to view the tympanogram, acoustic reflex, and otoacoustic reflex results. And a audiogram hyperlink 1072 to the audiogram allows the operator to view the audiogram (e.g. chart 1022) by itself without the rest of the report.

Other aspects of the search result screen 1060 may include a plurality of checkboxes (shown generally at 1074), each checkbox corresponding to one of the reports listed, that allows the operator to select several reports. A compare button 1076 allows the operator to view a comparison of the reports that have been selected. Pressing this button brings up a compare screen 1080 that includes a comparison of the data charts from the selected reports, shown at 1082 and 1084, for the right and left ear of the patient. The charts 1082 and 1084 are computer-generated charts that show a comparison of the patient's performance for a particular test (e.g., the air and bone conduction test). Similar comparisons may also be performed for other hearing related tests as well. In some embodiments, for the reports being compared, the older results will be displayed less prominently, and the newer results will be displayed more prominently. A comparison of the relevant data for the charts is also displayed (generally at 1086 and 1088), as well as some basic information (generally at 1090), including the patient's name, dates and times of the test, chart numbers, the physician, the tester, the clinic, and the elapsed time for the more recent test. A navigation button 1096 allows the operator to return to the previous screen.

While the invention has been described with respect to a number of specific embodiments, those skilled in the art will recognize that the innovative concepts described herein can be modified and varied over a wide range of applications. For example, although the multimedia user interface of the invention has been described in terms a number of discrete components, two or more of the components may be combined to form one or more super components, or one component may be divided into several sub-components. Accordingly, the scope of the invention should not be limited to any of the specific exemplary teachings discussed, but is instead defined by the following claims.

What is claimed is:

1. A computer-readable storage medium storing computer-readable instructions for a multimedia user interface for a computer-based automated hearing test, the computer-readable instructions comprising:
   a patient information component configured to allow an operator or a patient to enter the patient's information into the automated hearing test;
   a patient testing component configured to allow the patient to administer a hearing related test to himself, the patient testing component causing the patient to interact with the automated hearing test during the hearing related test; and
   a reporting component configured to present a result of the patient's hearing related test in a graphical format, the result including data from the patient information component and the patient testing component that are relevant for a hearing health professional to be able to assess the patient's hearing;
   wherein the patient testing component comprises a tympanogram, acoustic reflex, and otoacoustic emission test screen for performing tympanogram, acoustic reflex, and otoacoustic emission testing.

2. The computer-readable instructions of claim 1, wherein the patient information component comprises a new session screen for entering basic information about the patient.

3. The computer-readable instructions of claim 2, wherein the basic information includes patient name, patient chaff number, and patient testing language.

4. The computer-readable instructions of claim 2, wherein the new session screen includes a list of hearing related tests that may be selected.

5. The computer-readable instructions of claim 1, wherein the patient testing component comprises a pure tone threshold response screen for allowing the patient to respond during a pure tone threshold test.

6. The computer-readable instructions of claim 5, wherein the pure tone threshold response screen includes an on-screen button which the patient may press in response to hearing a tone.

7. The computer-readable instructions of claim 1, wherein the patient testing component comprises a patient survey screen for gathering hearing related information about the patient.

8. The computer-readable instructions of claim 1, wherein the reporting component comprises a report screen for displaying a report of the result of the patient's hearing test.

9. The computer-readable instructions of claim 8, wherein the report screen is adapted to be viewed as a web page using a web browser.

10. The computer-readable instructions of claim 9, wherein the web page of the report is adapted to be accessed from a network connection.

11. The computer-readable instructions of claim 8, wherein the report screen allows the report to be changed from a one-chart format to a two-chart format and vice versa.

12. The computer-readable instructions of claim 8, wherein the report screen allows the report to be printed on a one-page printout.

13. The computer-readable instructions of claim 8, wherein the reporting component further comprises a search screen for searching previously saved reports based on one or more search parameters.

14. The computer-readable instructions of claim 13, wherein the reporting component further comprises a results screen for listing previously saved reports that satisfy the one or more search parameters.

15. The computer-readable instructions of claim 13, wherein the reporting component further comprises a comparison screen for displaying a comparison of two reports, the comparison showing a recent report more prominently than an older report.

16. The computer-readable instructions of claim 1, further comprising a patient training component configured to instruct the patient regarding operation of the automated hearing test.

17. The computer-readable instructions of claim 16, wherein the patient training component comprises one or more screens for providing general information regarding the operation of the automated hearing test and one or more verbal information messages for each screen.

18. The computer-readable instructions of claim 16, wherein the patient training component comprises one or more screens for providing specific information regarding one or more hearing related tests of the automated hearing test and one or more verbal information messages for each screen.

19. The computer-readable instructions of claim 1, further comprising a patient management component configured to manage a progress of the patient during the automated hearing test.

20. The computer-readable instructions of claim 19, wherein the patient management component is further configured to notify a hearing health professional of equipment related problems during the hearing related test.

21. The computer-readable instructions of claim 19, wherein the patient management component comprises a progress indicator for indicating a progress of the patient during the hearing related test.

22. The computer-readable instructions of claim 1, further comprising a system configuration component configured to allow the operator to configure the automated hearing test.

23. The computer-readable instructions of claim 22, wherein the system configuration component comprises an input screen for inputting default information into the automated hearing test that is adapted to be used for all patients.

24. The computer-readable instructions of claim 22, wherein the system configuration component comprises a paging encoder screen for inputting paging encoder information into the automated hearing test that is adapted to be used for all patients.

25. The computer-readable instructions of claim 22, wherein the system configuration component comprises a paging options screen for defining one or more events for which the automated hearing test will page the operator.

26. The computer-readable instructions of claim 22, wherein the system configuration component comprises a test options screen for defining a name of each hearing related test performed by the automated hearing test.

27. The computer-readable instructions of claim 1, wherein the patient testing component comprises a speech reception threshold response screen for allowing the patient to respond during a speech reception threshold test.

28. The computer-readable instructions of claim 27, wherein the speech reception threshold response screen includes a set of picture-word pairs from which the patient may select one picture-word pair during the speech reception threshold test.

29. A computer-readable storage medium storing computer-readable instructions for a multimedia user interface for a computer-based automated hearing test, the computer-readable instructions comprising:

a patient information component configured to allow an operator or a patient to enter the patient's information into the automated hearing test;

a patient testing component configured to allow the patient to administer a hearing related test to himself, the patient testing component causing the patient to interact with the automated hearing test during the hearing related test; and a reporting component configured to present a result of the patient's hearing related test in a graphical format, the result including data from the patient information component and the patient testing component that are relevant for a hearing health professional to be able to assess the patient's hearing;

wherein the patient testing component comprises a speech discrimination response screen for allowing the patient to respond during a speech discrimination test.

30. The computer-readable instructions of claim 29, wherein the speech discrimination response screen includes multiple sets of picture-word pairs that are randomly presented one set at a time from which the patient may select one picture-word pair in response to hearing a word.

31. A computer-based automated hearing test, comprising:
- a display screen;
- a transducer; and
- a computer, said computer executing an automated hearing test thereon, said automated hearing test having a multimedia user interface configured to use the display screen and the transducer, said multimedia user interface comprising:
  - a system configuration component configured to allow an operator to configure the automated hearing test;
  - a patient information component configured to allow the operator or a patient to enter the patient's information to be entered into the automated hearing test;
  - a patient testing component configured to allow the patient to administer a hearing related test to himself, the patient testing component presenting audio and visual instructions for causing the patient to interact with the automated hearing test during the hearing related test; and
  - a reporting component configured to present a result of the patient's hearing related test in a graphical format, the result including data from the patient information component and the patient testing component that are relevant for a hearing health professional to be able to assess the patient's hearing.

32. The computer-based automated hearing test of claim 31, wherein the system configuration component comprises a computer identification screen for defining an identity of the computer, and a network options screen for setting up the computer to be connected to a network.

33. The computer-based automated hearing test of claim 31, wherein the system configuration component comprises an input screen for inputting default information into the automated hearing test that is adapted to be used for all patients, and a test options screen for defining a name of each hearing related test performed by the automated hearing test.

34. The computer-based automated hearing test of claim 31, wherein the system configuration component comprises a paging encoder screen for inputting paging encoder information into the automated hearing test that is adapted to be used for all patients, and a paging options screen for defining one or more events for which the automated hearing test will page the operator.

35. The computer-based automated hearing test of claim 31, wherein the patient information component comprises a new session screen for entering basic information about the patient, including patient name, patient chart number, and patient testing language, the new session screen including a list of hearing related tests that may be selected.

36. The computer-based automated hearing test of claim 31, wherein the patient testing component comprises a pure tone threshold response screen for allowing the patient to respond during a pure tone threshold test, the pure tone threshold response screen including an on-screen button which the patient may press in response to hearing a tone.

37. The computer-based automated hearing test of claim 31, wherein the patient testing component comprises a speech reception threshold response screen for allowing the patient to respond during a speech reception threshold test, the speech reception threshold response screen including a set of picture-word pairs from which the patient may select one picture-word pair during the speech reception threshold test.

38. The computer-based automated hearing test of claim 31, wherein the patient testing component comprises a speech discrimination response screen for allowing the patient to respond during a speech discrimination test, the speech discrimination response screen including multiple sets of picture-word pairs that are randomly presented one set at a time from which the patient may select one picture-word pair in response to hearing a word.

39. The computer-based automated hearing test of claim 31, wherein the patient testing component comprises a tympanogram, acoustic reflex, and otoacoustic emission test screen for performing tympanogram, acoustic reflex, and otoacoustic emission testing, and a patient survey screen for gathering hearing related information about the patient.

40. The computer-based automated hearing test of claim 31, wherein the reporting component comprises a report screen for displaying a report of the result of the patient's hearing test, said report screen allowing the report to be changed from a one-chart format to a two-chart format and vice versa.

41. The computer-based automated hearing test of claim 40, wherein the computer functions as a web server and the report screen is adapted to be viewed as a web page using a web browser and a network connection.

42. The computer-based automated hearing test of claim 40, wherein the report screen allows the report to be printed on a one-page printout.

43. The computer-based automated hearing test of claim 40, wherein the reporting component further comprises a search screen for searching previously saved reports based on one or more search parameters, and a results screen for listing previously saved reports that satisfy the one or more search parameters.

44. The computer-based automated hearing test of claim 40, wherein the reporting component further comprises a comparison screen for displaying a comparison of two reports, the comparison showing a recent report more prominently than an older report.

45. The computer-based automated hearing test of claim 31, further comprising a patient training component configured to instruct the patient regarding operation of the automated hearing test.

46. The computer-based automated hearing test of claim 45, wherein the patient training component comprises one or more screens for providing general information regarding the operation of the automated hearing test and specific information regarding one or more hearing related tests, including one or more verbal information messages for each screen.

47. The computer-based automated hearing test of claim 31, further comprising a patient management component configured to manage a progress of the patient during the automated hearing test.

48. The computer-based automated hearing test of claim 47, wherein the patient management component is further configured to notify a hearing health professional of equipment related problems during the hearing related test, and a progress indicator for indicating a progress of the patient during the hearing related test.

49. A computer-readable storage medium storing computer-readable instructions for a multimedia user interface for a computer-based automated hearing test, the computer-readable instructions comprising:

a patient information component configured to allow an operator or a patient to enter the patient's information into the automated hearing test;

a system configuration component configured to allow an operator to configure the automated hearing test;

a tympanogram/acoustic reflex component configured to allow the operator to obtain a tympanogram and acoustic reflex measurement for the patient;

a patient training component configured to instruct the patient regarding operation of the automated hearing test;

a patient testing component configured to allow the patient to interact with the automated hearing test during a hearing related test;

a patient management component configured to manage the patient during the automated hearing test; and a reporting component configured to present a result of the patient's hearing test.

\* \* \* \* \*